US009066885B2

(12) United States Patent
Raghavan et al.

(10) Patent No.: US 9,066,885 B2
(45) Date of Patent: Jun. 30, 2015

(54) ADVANCED FUNCTIONAL BIOCOMPATIBLE POLYMERIC MATRIX CONTAINING NANO-COMPARTMENTS

(75) Inventors: Srinivasa R. Raghavan, Silver Spring, MD (US); Gregory F. Payne, Cockeysville, MD (US); Chao Zhu, McLean, VA (US); Matthew B. Dowling, Washington, DC (US)

(73) Assignee: University of Maryland, College Park, College Park, MA (US)

( * ) Notice: Subject to any disclaimer, the term of this patent is extended or adjusted under 35 U.S.C. 154(b) by 569 days.

(21) Appl. No.: 12/077,173

(22) Filed: Mar. 17, 2008

(65) Prior Publication Data

US 2008/0254104 A1    Oct. 16, 2008

Related U.S. Application Data

(60) Provisional application No. 60/895,221, filed on Mar. 16, 2007.

(51) Int. Cl.
| | | |
|---|---|---|
| A61P 17/02 | (2006.01) | |
| A61K 9/70 | (2006.01) | |
| A61K 9/127 | (2006.01) | |
| A61K 47/48 | (2006.01) | |

(52) U.S. Cl.
CPC .............. *A61K 9/7007* (2013.01); *A61K 9/127* (2013.01); *A61K 9/1271* (2013.01); *A61K 47/4823* (2013.01); *A61K 47/48769* (2013.01)

(58) Field of Classification Search
CPC ........ C08L 5/08; C08L 89/00; C08L 2666/02
See application file for complete search history.

(56) References Cited

U.S. PATENT DOCUMENTS

| | | | |
|---|---|---|---|
| 4,532,134 A | 7/1985 | Malette et al. | |
| 4,572,906 A | 2/1986 | Sparkes et al. | |
| 4,752,466 A | 6/1988 | Saferstein et al. | |
| 4,895,724 A | 1/1990 | Cardinal et al. | |
| 5,243,094 A | 9/1993 | Borg | |
| 5,426,182 A | 6/1995 | Jenkins et al. | |
| 5,900,479 A | 5/1999 | Glasser et al. | |
| 5,919,574 A | 7/1999 | Hoagland | |
| 6,140,089 A | 10/2000 | Aebischer et al. | |
| 6,371,975 B2 | 4/2002 | Cruise et al. | |
| 6,458,147 B1 | 10/2002 | Cruise et al. | |
| 6,548,081 B2 | 4/2003 | Sadozai et al. | |
| 6,602,952 B1 | 8/2003 | Bentley et al. | |
| 6,663,653 B2 | 12/2003 | Akerfeldt | |
| 6,827,727 B2 | 12/2004 | Stalemark et al. | |
| 6,830,756 B2 | 12/2004 | Hnojewyj | |
| 6,864,245 B2 | 3/2005 | Vournakis et al. | |
| 6,890,344 B2 | 5/2005 | Levinson | |
| 6,899,889 B1 | 5/2005 | Hnojewyj et al. | |
| 6,949,114 B2 | 9/2005 | Milo et al. | |
| 6,958,325 B2 | 10/2005 | Domb | |
| 6,994,686 B2 | 2/2006 | Cruise et al. | |
| 6,995,137 B2 | 2/2006 | You et al. | |
| 7,247,314 B2 | 7/2007 | Hnojewyj et al. | |
| 7,279,001 B2 | 10/2007 | Addis et al. | |
| 7,288,532 B1 | 10/2007 | Payne et al. | |
| 7,318,933 B2 | 1/2008 | Hnojewyj | |
| 7,351,249 B2 | 4/2008 | Hnojewyj et al. | |
| 7,482,503 B2 | 1/2009 | Gregory et al. | |
| 7,820,872 B2 | 10/2010 | Gregory et al. | |
| 8,664,199 B2 | 3/2014 | Dowling et al. | |
| 8,668,899 B2 | 3/2014 | Dowling et al. | |
| 2002/0028181 A1 | 3/2002 | Miller et al. | |
| 2002/0042473 A1 | 4/2002 | Trollsas et al. | |
| 2002/0068151 A1 | 6/2002 | Kim et al. | |
| 2004/0001893 A1* | 1/2004 | Stupp et al. .................. 424/488 |
| 2005/0038369 A1 | 2/2005 | Gregory et al. | |
| 2005/0147656 A1 | 7/2005 | McCarthy et al. | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0269485 A1 | 11/2006 | Friedman et al. | |
| 2007/0055364 A1* | 3/2007 | Hossainy et al. ............ 623/1.38 |

(Continued)

FOREIGN PATENT DOCUMENTS

EP    1222926    7/2002

OTHER PUBLICATIONS

Hou et al. "Preparation and characterization of RGD-immobilized chitosan scaffolds", Biomaterials 26 (2005) 3197-3206, published Oct. 14, 2004.*
Raghavan, et al. "Vesicle-Biopolymer Gels: Networks of Surfactant Vesicles Connected by Associating Biopolymers". Langmuir 2005, 21, 26-33.*
Li, et al. "Multivesicular Liposomes for Oral Delivery of Recombinant Human Epidermal Growth Factor." Archives of Pharmacal Research, 2005, 28, 8, 988-994.*
Chiaki Yoshina-Ishii and Steven G. Boxer, Arrays of Mobile Tethered Vesicles on Supported Lipid Bilayers, J. Am. Chem. Soc. 125(13):3696-3697 (2003).

(Continued)

*Primary Examiner* — Audrea Buckley
(74) *Attorney, Agent, or Firm* — The Morales Law Firm; Joseph L. Morales

(57) ABSTRACT

The present invention provides a novel biomaterial which is a hybrid, self-assembling biopolymeric networked film that is functionalized through hydrophobic interactions with vesicles loaded with bioactive agents. The biomaterial compound is a polymeric network of hydrophobically modified chitosan scaffolds that is taken from solution and formed as a solid film. This solid state film is capable of hydrophobic interactions with the functionalized vesicles. The vesicles include one or more lamellar structures forming one or more nano-compartments that are capable of containing similar or alternative active moieties within. Use of the film results in a degradation of the chitosan scaffold thereby releasing the active moieties within the vesicles from the scaffold. Application of the current invention occurs through various delivery mechanisms and routes of administration as will be described herein.

21 Claims, 14 Drawing Sheets

(56) References Cited

U.S. PATENT DOCUMENTS

| | | | |
|---|---|---|---|
| 2007/0148215 | A1 | 6/2007 | Teslenko et al. |
| 2008/0103228 | A1 | 5/2008 | Falcone et al. |
| 2008/0254104 | A1 | 10/2008 | Raghavan et al. |
| 2009/0062849 | A1 | 3/2009 | Dowling |
| 2009/0192429 | A1 | 7/2009 | Daniels et al. |
| 2009/0226391 | A1 | 9/2009 | Roberts et al. |
| 2011/0052665 | A1 | 3/2011 | Hardy et al. |
| 2011/0217785 | A1 | 9/2011 | Liu et al. |
| 2011/0280857 | A1 | 11/2011 | Dowling et al. |
| 2012/0058970 | A1 | 3/2012 | Dowling |
| 2012/0252703 | A1 | 10/2012 | Dowling |

OTHER PUBLICATIONS

Yoshina-Ishii et al., General Method for Modification of Liposomes for Encoded Assembly on Supported Bilayers, J. Am. Chem. Soc. 127(5):1356-1357 (2005).

Yoshina-Ishii et al., Diffusive Dynamics of Vesicles Tethered to a Fluid Supported Bilayer by Single-Particle Tracking, Langmuir 22(13):5682-5689 (2006).

Esquenet et al., Structural and Rheological Properties of Hydrophobically Modified Polysaccharide Associative Networks, Langmuir 20(9):3583-3592 (2004).

Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

Boukobza et al., Immobilization in Surface-Tethered Lipid Vesicles as a New Tool for Single Biomolecule Spectroscopy, J. Phys. Chem. B 105(48):12165-12170 (2001).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Khan et al., Mechanical, Bioadhesive Strength and Biological Evaluations of Chitosan Films for Wound Dressing, J. Pharm. Pharmaceut. Sci. 3(3):303-311 (2000).

Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).

Anderluh et al., Properties of Nonfused Liposomes Immobilized on an L1 Biacore Chip and Their Permeabilization by a Eukaryotic Pore-forming Toxin, Anal. Biochem. 344:43-52 (2005).

New! Pioneer Chip L1 Improved binding studies in model membrane systems, BIA Journal No. 2 1998.

Lunelli et al., Covalently Anchored Lipid Structures on Amine-Enriched Polystyrene, Langmuir 21(18):8338-8343 (2005).

Kjoniksen et al., Light Scattering Study of Semidilute Aqueous Systems of Chitosan and Hydrophobically Modified Chitosans, Macromolecules 31(23):8142-8148 (1998).

Wu et al., Voltage-Dependent Assembly of the Polysaccharide Chitosan onto an Electrode Surface, Langmuir 18 (22):8620-8625 (2002).

Fernandes et al., Electrochemically Induced Deposition of a Polysaccharide Hydrogel onto a Patterned Surface, Langmuir 19(10):4058-4062 (2003).

Wu et al., Spatially Selective Deposition of a Reactive Polysaccharide Layer onto a Patterned Template, Langmuir 19 (3):519-524 (2003).

Zhu et al., Reversible Vesicle Restraint in Response to Spatiotemporally Controlled Electrical Signals: A Bridge between Electrical and Chemical Signaling Modes, Langmuir 23(1) 286-291 (2007).

Gregory F. Payne and Srinivasa R. Raghavan, Chitosan: a Soft Interconnect for Hierarchical Assembly of Nano-scale Components, Soft Matter 3:521-527 (2007).

Lee et al., Vesicle-Biopolymer Gels: Networks of Surfactant Vesicles Connected by Associating Biopolymers, Langmuir 21(1):26-33 (2005).

Zhu et al., Bioinspired Vesicle Restraint and Mobilization Using a Biopolymer Scaffold, Langmuir 22(7):2951-2955 (2006).

Lee et al., Transition from Unilamellar to Bilamellar Vesicles Induced by an Amphiphilic Biopolymer, Phys. Review Letters, 96:048102-1-048102-4 (2006).

Desbrieres et al., Hydrophobic Derivatives of Chitosan: Characterization and Rheological Behaviour, Biological Macromolecules, 19:21-28 (1996).

Cooper et al., A Vesicle Capture Sensor Chip for Kinetic Analysis of Interactions with Membrane-Bound Receptors, Anal. Biochem. 277:196-205 (2000).

Tangpasuthadol, Surface Modification of Chitosan Films. Effects of Hydrophobicity on Protein Adsorption, Carbohydrate Res. 338:937-942 (2003).

Stavroula Sofou and James L. Thomas, Stable Adhesion of Phospholipid Vesicles to Modified Gold Surfaces, Biosensors and Bioelectronics 18:445-455 (2003).

Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).

Paul S. Cremer and Steven G. Boxer, Formation and Spreading of Lipid Bilayers on Planar Glass Supports, J. Phys. Chem. B 103(13):2554-2559 (1999).

Li et al., Multivesicular Liposomes for Oral Delivery of Recombinant Human Epidermal Growth Factor, Arch Pharm Res 28(8):988-994 (2005).

Koehler et al., Microstructure and Dynamics of Wormlike Micellar Solutions Formed by Mixing Cationic and Anionic Surfactants, J. Phys. Chem. B 104(47):11035-11044 (2000).

Kaler et al., Spontaneous Vesicle Formation in Aqueous Mixtures of Single-Tailed Surfactants, Science 245(4924): 1371-1374 (1989).

Kaler et al., Phase Behavior and Structures of Mixtures of Anionic and Catlonlc Surfactants, J. Phys. Chem. 96(16): 6698-6707 (1992).

Fu et al., Protein stability in controlled-release systems, Nature Biotechnology 18:24-25 (2000).

D. D. Lasic and D. Papahadjopoulos, Liposomes Revisited, Science 267(5202):1275-1276 (1995).

Dan D. Lasic, Novel Applications of Liposomes, Trens in Biotechnology (TIBTECH) 16:307-321 (1998).

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Naumann et al., Proton Transport Through a Peptide-tethered Pilayer Lipid Membrane by the H+-ATP Synthase from Chloroplasts Measured by Impedance Spectroscopy, Biosensors and Bioelectronics 17:25-34 (2002).

Nikolelis et al., A Minisensor for the Rapid Screening of Sucralose Based on Surface-stabilized Bilayer Lipid Membranes, Biosensors & Bioelectronics 15:439-444 (2000).

Mathivet et al., Shape Change and Physical Properties of Giant Phospholipid Vesicles Prepared in the Presence of an AC Electric Field, Biophysical Journal 70:1112-1121 (1996).

Puu et al., Retained Activities of Some Membrane Proteins in Stable Lipid Bilayers on a Solid Support, Biosensors and Bioelectronics 10:463-476 (1995).

Szymanska et al., Fullerene Modified Supported Lipid Membrane as Sensitive Element of Sensor for Odorants, Biosensors & Bioelectronics 16:911-915 (2001).

Rongen et al., Liposomes and Immunoassays, J. Immunol. Methods 204:105-133 (1997).

Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).

Zhdanov et al., Comments on Rupture of Adsorbed Vesicles (Langmuir 2001, 17, 3518-3521).

Zhdanov et al. Adsorption and Spontaneous Rupture of Vesicles Composed of Two Types of Lipids (Langmuir 2006, 22, 3477-3480).

(56) References Cited

OTHER PUBLICATIONS

Dimitrievski et al., Influence of Lipid-Bilayer-Associated Molecules on Lipid-Vesicle Adsorption (Langmuir 2010, 26 (8), 5706-5714).

Allerbo et al., Simulation of lipid vesicle rupture induced by an adjacent supported lipid bilayer patch (Colloids and Surfaces B: Biointerfaces 2011, 82, 632-636).

Dimitrievski et al., Simujlations of Lipid Vesicle Adsorption for Different Lipid mixtures (Langmuir 2008, 24, 4077-4091).

Angelova, M. I.; Dimitrov, D. S. "Liposome electroformation." Faraday Discuss. 1986, 81, 303-306.

Arnaud, F.; Teranishi, K.; Tomori, T.; Carr, W.; McCarron, R. "Comparison of 10 hemostatic dressings in a groin puncture model in swine." J. Vascular Surg. 2009, 50, 632-639.

Bochicchio, G.; Kilbourne, M.; Kuehn, R.; Keledjian, K.; Hess, J.; Scalea, T. "Use of a modified chitosan dressing in a hypothermic coagulopathic grade V liver injury model." Am. J. Surg. 2009, 198, 617-622.

Champion, H. R.; Bellamy, R. F.; Roberts, C. P.; Leppaniemi, A. "A profile of combat injury." J. Trauma2003, 54, S13-S19.

Christensen, S. M.; Stamou, D. "Surface-based lipid vesicle reactor systems: fabrication and applications." Soft Matter 2007, 3, 828-836.

Chenite, A. et al "Rheological characterization of thermogelling chitosan/glycerol-phosphate solutions" Carbohydrate Polymers 46, 39-47 (2001).

Coster, Bag-On-Valve Series Offers Faster Filling and Better Drop Resistance. 2007. Downloaded from the world wide web on Jan. 18, 2012 <http://www.coster.com/news/eng/2007-10-18_AE_bov/AE_Manchester_BOV_eng_pdf.>.

Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." J. Am. Chem. Soc.2008, 130, 6267-6271.

Doolittle, R. F. "Fibrinogen and fibrin." Annu. Rev. Biochem. 1984, 53, 195-229.

Dowling, M.B., et al. "A self-assembling hydrophobically modified chitosan capable of reversible hemostatic action." Biomaterials. May 2011 Vo. 31, pp. 3351-3357.

Durian, Douglas J., et al. "Making a frothy shampoo or beer." Physics Today. pp. 62-63. May 2010.

Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision." Proc. Natl. Acad. Sci. U. S. A. 2006, 103, 5054-5059.

Ellis-Behnke, R. G.; Liang, Y.-X.; Tay, D. K. C.; Kau, P. W. F.; Schneider, G. E.; Zhang, S.; Wu, W.; So, K.-F. "Nano hemostat solution: Immediate hemostasis at the nanoscale." Nanomedicine 2006, 2, 207-215.

GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.pdf>.

Hirano and Noishiki, The Blood Compatibility of Chitosan and N-Acylchitosans, J. Biochem. Materials Res. 413-417 (1985).

Kauvar, D. S.; D S.. Lefering R.; Wade, C. E. "Impact of hemorrhage on trauma outcome: An overview of epidemiology, clinical presentations, and therapeutic considerations." J. Trauma 2006, 60, S3-S9.

Kean, T.; Thanou, M. "Biodegradation, biodistribution and toxicity of chitosan." Adv. Drug Deliv. Rev. 2010,62, 3-11.

Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." J. Trauma 2009, 67, 450-460.

Kim, Seung-Ho MD; Stezoski, S. William; Safar, Peter MD; Capone, Antonio MD; Tisherman, Samuel MD. "Hypothermia and Minimal Fluid Resuscitation Increase Survival after Uncontrolled Hemorrhagic Shock in Rats" Journal of Trauma-Injury Infection & Critical Care. 42(2):213-222, Feb. 1997.

Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." J. Biotechnol. 2000, 74, 137-58.

Kubota, et al. Gelation Dynamics and Gel Structure Fibrinogen, Colloids Surf. B. Biointerfaces 38:103-109 (2004).

Larson, M. J.; Bowersox, J. C.; Lim, R. C.; Hess, J. R. "Efficacy of a fibrin hemostatic bandage in controlling hemorrhage from experimental arterial injuries." Arch. Surg. 1995, 130, 420-422.

Lew, W. K.; Weaver, F. A. "Clinical use of topical thrombin as a surgical hemostat." Biologics 2008, 2, 593-599.

Lu, S. et al. "Preparation of Water-Soluble Chitosan" Journal of Applied Polymer Science 91, 3497-2503 (2004).

Macfarlane, R. G. "An enzyme cascade in the blood dotting mechanism, and its function as a biological amplifier." Nature 1964, 202, 498-499.

Naumann, C. A.; Prucker, O.; Lehmann, T.; Ruhe, J.; Knoll, W.; Frank, C. W. "The polymer-supported phospholipid bilayer: Tethering as a new approach to substrate-membrane stabilization." Biomacromolecules2002, 3, 27-35.

Neuffer, M. C.; McDivitt, J.; Rose, D.; King, K.; Cloonan, C. C.; Vayer, J. S. "Hemostatic dressings for the first responder: A review." Military Med. 2004, 169, 716-720.

Pusateri, A. E.; Holcomb, J. B.; Kheirabadi, B. S.; Alam, H. B.; Wade, C. E.; Ryan, K. L. "Making sense of the preclinical literature on advanced hemostatic products." J. Trauma 2006, 60, 674-682.

Raghavan, S. R.; Cipriano, B. H. Gel formation: Phase diagrams using tabletop rheology and calorimetry. InMolecular Gels; Weiss, R. G., Terech, P., Eds.; Springer: Dordrecht, 2005; pp. 233-244.

Rao, S. B.; Sharma, C. P. "Use of chitosan as a biomaterial: Studies on its safety and hemostatic potential." J. Biomed. Mater. Res. 1997, 34, 21-28.

Redepenning, J. et al. "Electrochemical preparation of chitosan/hydroxyapatite composite coatings on titanium substrates." Journal of Biomedical Materials Research. vol. 66A. pp. 411-416. 2003.

Reiss, R. F.; Oz, M. C. "Autologous fibrin glue: Production and clinical use." Transfusion Med. Rev. 1996, 10, 85-92.

Rodriguez, M.S., et al "Interaction between chitosan and oil under stomach and duodenal digestive chemical conditions" Biosci. Biotechnol. Biochem. 69 (11), 2057-2062 (2005).

Stewart, R. M.; Myers, J. G.; Dent, D. L; Ermis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: The argument for injury prevention." J. Trauma 2003, 54, 66-70.

Szejtli, J. "Introduction and general overview of cyclodextrin chemistry." Chem. Rev. 1998, 98, 1743-1753.

Tanaka, M.; Sackmann, E. "Polymer-supported membranes as models of the cell surface." Nature 2005,437, 656-663.

Tonelli, A. E. "Nanostructuring and functionalizing polymers with cyclodextrins." Polymer 2008, 49, 1725-1736.

Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.

Kurth, Dirk G. and Thomas Bein. "Monomolecular Layers and Thin Films of Silane Coupling Agents by Vapor-Phase Adsorption on Oxidized Aluminum." J. Phys. Chem. 1992. 96. 6707-6712.

US Office Action issued in related U.S. Appl. No. 12/231,571 on Mar. 5, 2012.

US Office Action issued in related U.S. Appl. No. 12/946,818 on Jan. 28, 2013.

US Notice of Allowance issued in related U.S. Appl. No. 12/946,818 on Oct. 29, 2013.

US Office Action issued in related U.S. Appl. No. 13/209,399 on Mar. 1, 2013.

US Office Action issued in related U.S. Appl. No. 13/310,579 on Apr. 11, 2013.

Alam, Hasan B. et al., Comparative Analysis of Hemostatic Agents in a Swine Model of Lethal Groin Injury, J. Trauma 54:1077-1082 (2003).

(56) References Cited

OTHER PUBLICATIONS

Brandenberg, Greg et al., Chitosan: A New Topical Hemostatic Agent for Diffuse Capillary Bleeding in Brain Tissue, Neurosurgery 15(1): 9-13 (1984).

Malette, William G. et al., Chitosan: A New Hemostatic, The Annals of Thoracic Surgery 36(1):55-58 (1983).

Burkatovskaya, Marina et al., Use of Chitosan Bandage to Prevent Fatal Infections Developing From Highly Contaminated Wounds in Mice, Biomaterials 27:4157-4164 (2006).

Kozen, Buddy G. et al., An Alternative Hemostatic Dressing: Comparison of CELOX, HemCon, and QuikClot, Acad. Emerg. Med. 15:74-81(2008).

Whang, Hyun Suk et al., Hemostatic Agents Derived from Chitin and Chitosan, J. Macromolecular Science 45:309-323 (2005).

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

Meier, Wolfgang et al., Vesicle and Cell Networks: Interconnecting Cells by Synthetic Polymers, Langmuir 12:5028-5032 (1996).

International Search Report issued in corresponding PCT Application No. PCT/US2014/025896 on Aug. 19, 2014.

European Search Report issued in corresponding application No. 10830878 on May 28, 2014.

* cited by examiner

ADVANCED FUNCTIONAL BIOCOMPATIBLE POLYMERIC MATRIX CONTAINING NANO-COMPARTMENTS

CROSS REFERENCE TO RELATED APPLICATION

The present application claims priority under 35 U.S.C. §119 to the U.S. Provisional Application Ser. No. 60/895,221, filed on Mar. 16, 2007, which is herein incorporated by reference in its entirety.

FIELD OF THE INVENTION

The present invention generally relates to the field of biopolymers and particularly to hydrophobic modification of biopolymers for solid state film formation and the association of these biopolymers with vesicles (liposomes).

BACKGROUND OF THE INVENTION

A derivative of glucose found throughout the natural world, Chitin $(C_8H_{13}O_5N)_n$, nature's second most abundant compound next to cellulose, is naturally found as a polysaccharide or long-chain polymer composed of repeating monomeric units of N-acetylglucosamine in beta-1,4 linkage.

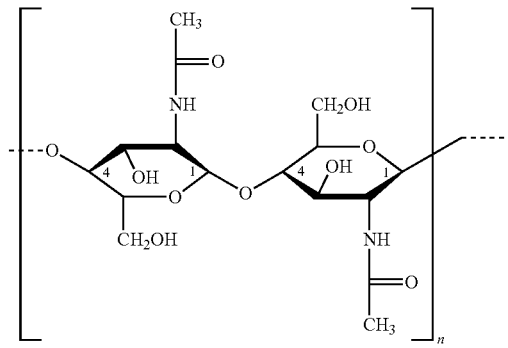

Chitin structure showing two of the repeating N-Acetylglucosamine

Chitin is a non-toxic, biocompatible and biodegradable polymer that serves a structural function and contributes strength to those structures of which it is a component feature. For instance, chitin is a main component found in the shells (exoskeletons) of various animals like crab, lobster, and shrimp (crustaceans); ants, beetles, and butterflies (insects); the beaks of squid and octopi (cephalopods); and the cell walls of fungi, to name a few. Chitin has been used for industrial, medicinal, agricultural, cosmetic, and numerous other purposes providing advantageous characteristics in these various settings.

Chitosan is a deacetylated derivative of chitin that retains the non-toxic, biocompatible and biodegradable characteristics of its parent. Chitosan is a linear polysaccharide composed of repeating β-(1-4)-linked D-glucosamine monomeric units. Chitosan and its derivatives have been widely studied for their potential applications in various fields, such as industry, medicine, biotechnology, cosmetics and agriculture due to their generally acidic characteristics and their readily reactive nature.

Nanotechnology is the name most often associated with the field of applied science and technology that aims to control matter on the atomic and molecular scale. Thus, typical size ranges for the components being worked with and "devices" being constructed range from 1 to 100 nanometers. The "devices" may be anything from mechanical, to chemical, to biological constructs. Nano-robots that can perform tasks through physical movement and manipulation of their surrounding environment and nano-therapeutics that are synthesized within biomaterial constructs to provide biologically active molecular components/active moieties and thus provide chemical/biological interaction with their surrounding environment are just a couple of the numerous and varied examples of the current application of nanotechnology. Today many such "nano-constructs" are known and being employed in numerous fields to accomplish various tasks.

Vesicles are hollow spherical structures, that may be nano-scale in size, formed by the self-assembly of surfactants, lipids, or block copolymers in aqueous solution. They have long been a scientific curiosity because of their structural resemblance to primitive biological cells. More importantly, vesicles are of technological interest for application ranging from drug delivery and controlled release to bioseparations and sensing. Many of these applications rely upon the ability of vesicles to entrap desired chemicals (i.e., functionalization) in their interior and thereafter release these chemicals to the external medium in a controlled manner. Thus, vesicles, (e.g. liposomes, in the case of lipids being the substituent molecules), as defined by their membrane structures, play many roles in the world of chemical and organic reactions.

Currently, the use of various biopolymer backbones, such as chitosan lattices/networks or other polysaccharide/polypeptide networks, in combination with functionalized vesicle/liposomes are known to be useful bioactive complexes for numerous applications which may be contained/loaded in vesicle/liposome structures. Therefore, it would be desirable to provide novel bioactive complexes that were able to promote increased ease of these bioactive complexes formation and increased functionality of such complexes.

SUMMARY OF THE INVENTION

The current invention is a novel hybrid composition of matter. In preferred exemplary embodiments, the composition of matter is networked film matrix of hydrophobically modified biopolymer (chitosan) backbone that hydrophobically interacts, in a self assembling manner, with vesicles (liposomes or micelles) that may be functionalized. In other preferred exemplary embodiments, the current invention provides a system and kit that utilize the novel film matrix. In still further preferred exemplary embodiments, novel methods of constructing and using the film matrix of the current invention are provided.

In a first preferred exemplary embodiment, the film is a solid-state matrix of hydrophobically modified chitosan (the "hm-Chitosan film"). This readily reactive matrix, in a second preferred exemplary embodiment of the current invention, is capable of being functionalized, through the attachment of vesicles (liposomes and/or micelles) to form a solid-state, functionalized biopolymer networked film (the "functionalized film"). The vesicles may be empty "sacs" or may be functionalized in various manners, including containing various bioactive agents or moieties either as part of the membrane layer or stored within an interior cavities or environments. The size of these vesicles and/or the storage locations for the bioactive agents within may be on a nano-scale or larger.

The exemplary systems may include either the hm-Chitosan film or functionalized film being employed within a particular environment. For instance, the system may be a wound healing system where the functionalized film is provided as an elastic, flexible "wrap" that may be placed in direct contact with the wounded area or location. The novel films and systems have many important features, for example: 1. the readily reactive hydrophobically modified biopolymeric network film that provides a wide range of functionalization options and capabilities when functionalized by interaction with vesicles, such as liposomes; and 2. the diverse variety of bioactive agents (molecules) of interest that may be loaded into the nano-compartments of the liposomes for packaging and release into a determined environment.

It is also another preferred exemplary embodiment of the current invention to provide a method of forming or fabricating a biopolymer film that includes complexing a biopolymer with an amphiphilic compound (hydrophilic heads and hydrophobic tails), and then dehydrating the hydrophobically modified biopolymer into a solid state film. The solid state is preferably a film matrix of amphiphilic biopolymers (hm-Chitosan). The current invention may be further exemplified by the preferred embodiment wherein the solid state matrix is functionalized by interaction with functional vesicles or liposomes including bioactive agents or moieties. The functionalization of the solid state matrix with the biologically active liposomes may preferably occur by hydrophobic interaction between the hydrophobic tail of the hm-Chitosan film matrix and vesicles/liposomes. Another exemplary functional result may be that the liposomes serve to cross-link the hm-Chitosan matrix that constitute the film.

In another exemplary preferred embodiment of the current invention, a method of using a hm-Chitosan film is provided. The hm-Chitosan film for use in this method includes a matrix of hydrophobically modified chitosan biopolymers that are presented in a solid state film. The method of using this solid state hm-Chitosan film matrix includes, in an exemplary preferred embodiment, interacting the hm-Chitosan film with a liposome (vesicle) containing solution, whereby hydrophobic interaction allows for the self-assembly of a functionalized film. Another exemplary method of use may include the application of the functionalized film to an area whereby active ingredients stored by or contained within the liposomes may be released to perform their function.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1A:
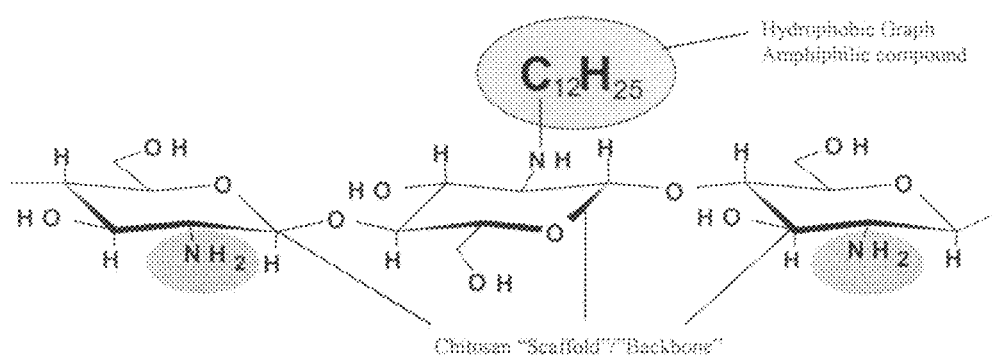
FIGS. 1A and 1B are structural and graphical representations of a hydrophobically modified chitosan (hm-Chitosan) biopolymer film in accordance with an exemplary embodiment of the current invention.
Figure 1B:
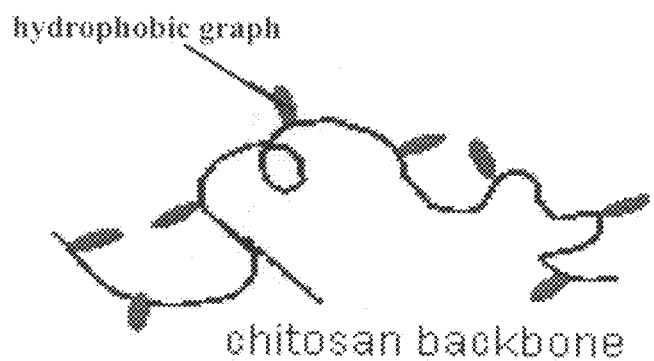
Figure 2:
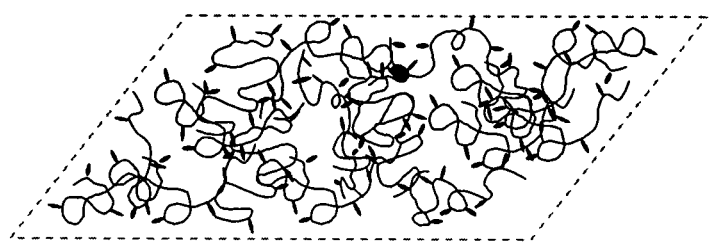
FIG. 2 is an illustration representing a readily reactive, dehydrated, solid state hm-Chitosan film matrix, wherein the hm-chitosan "backbone" or "scaffold" is capable of being cast into a film and the amphiphilic compounds allow for hydrophobic interaction with vesicles or liposomes to provide a functionalized film in accordance with an exemplary embodiment of the present invention.

Referring generally now to FIGS. 1 through 11, exemplary embodiments of the present invention are shown. In preferred embodiments, a novel solid-state, hm-Chitosan film matrix including numerous hydrophobically modified chitosan compounds, is shown in FIGS. 1A, 1B, and 2. These novel compounds consist of a biopolymer (e.g., chitosan) backbone that includes a hydrophilically reactive functional group (e.g., amino groups) that binds with the hydrophilically reactive head groups (e.g., carbonyl functional group) of an amphiphilic compound (e.g., aldehyde). The head group is further associated with a hydrophobic tail group. In the current embodiment, the hydrophobic tail may be for example a hydrocarbon. Thus, a hydrophobic tail is associated with the biopolymer's chitosan backbone providing the hydrophobic modification to the molecule that extends from the backbone and may interact with the surrounding environment in numerous ways, such as through hydrophobic interaction with other hydrophobic tails on the backbone or through hydrophobic interaction with other molecules and/or structures. Typically, and for the purposes of the preferred embodiments of the instant application, these hydrophobically modified polymers (biopolymers) are referenced as being composed of a chitosan "backbone", "scaffold", and/or "lattice". Thus, the backbone of the hydrophobically modified biopolymer film matrix of the preferred embodiments of the current invention is the biopolymer chitosan. Other biopolymers which include similar characteristics of the chitosan backbone may be employed with departing from the scope and spirit of the instant invention.

Chitosan is a deacetylated derivative of chitin, wherein the degree of deacetylation (% DA) may range from 60-100% and determines the charge density. Chitosan is a linear polysaccharide composed of repeating β-(1-4)-linked D-glucosamine monomeric units.

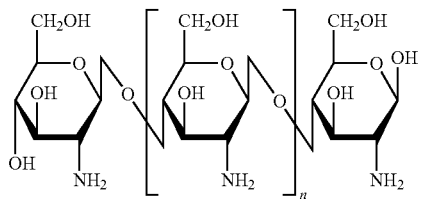

Chitosan structure showing three of the repeating beta-(1-4)-linked D-glucosamine units (deacetylated)

These repeating monomeric units include a free amino group (functional group) and may make molecules or compounds containing chitosan or its derivatives readily reactive. The hydrophobic modification of the chitosan backbone is through the association of an amphiphilic compound with the amino group, such that the hydrophobic tail of the amphiphilic compound is bound with the hydrophilic backbone structure. As seen in FIGS. 1B and 2, this hydrophobically modified chitosan backbone (hm-Chitosan) may then be cast into a film. In the preferred embodiment of FIG. 2, numerous hm-Chitosan backbones may fill a solution which may then be cast into a film forming the novel hm-Chitosan film of the current invention. This film matrix is a solid-state or dried film of the hm-Chitosan.

Figure 6:
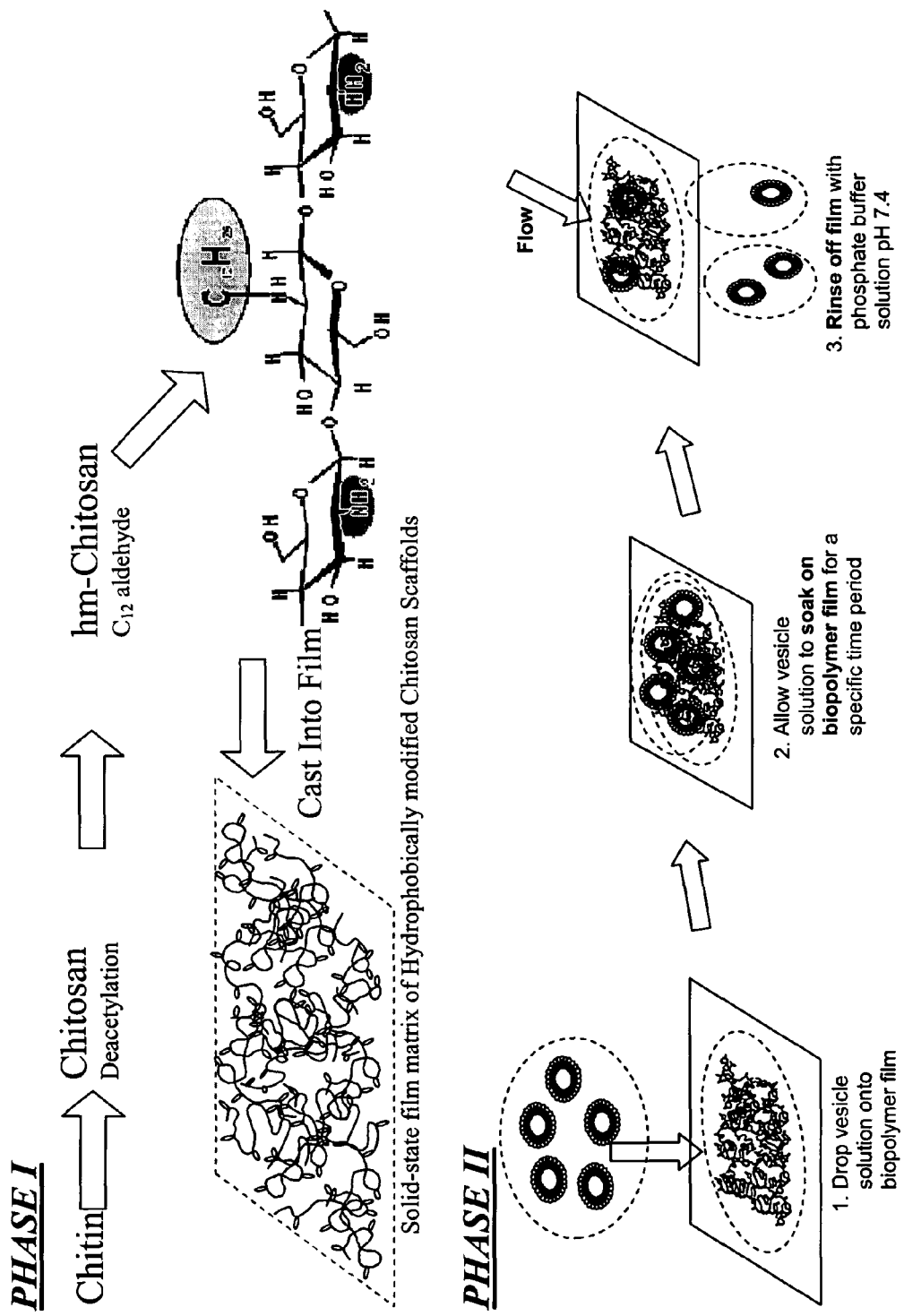
FIG. 6 is an illustration of the two phases of formation of the novel composition of matter of the current invention. PHASE I: a formation or fabrication process of the solid-state, hm-Chitosan film matrix; PHASE II: a formation or fabrication process of a functionalized film of the current invention, wherein the hm-Chitosan film matrix from PHASE I is used to form this secondary composition of matter.

In a preferred embodiment shown in FIGS. 6 (PHASE I) the formation or fabrication of this novel solid-state, hm-Chitosan film matrix is graphically represented. Thus, a first novel, preferred embodiment of the current invention is a dried, hm-Chitosan film or composition of matter which may be readily reactive with additional molecules and/or compounds. It is preferred that this composition of matter be prepared as a readily reactive, solid-state film matrix for application and use in various environments. However, various other implementation states of the current invention as may be contemplated by those of ordinary skill in the art are hereby assumed to fall within the scope of the current invention.

Figure 3:
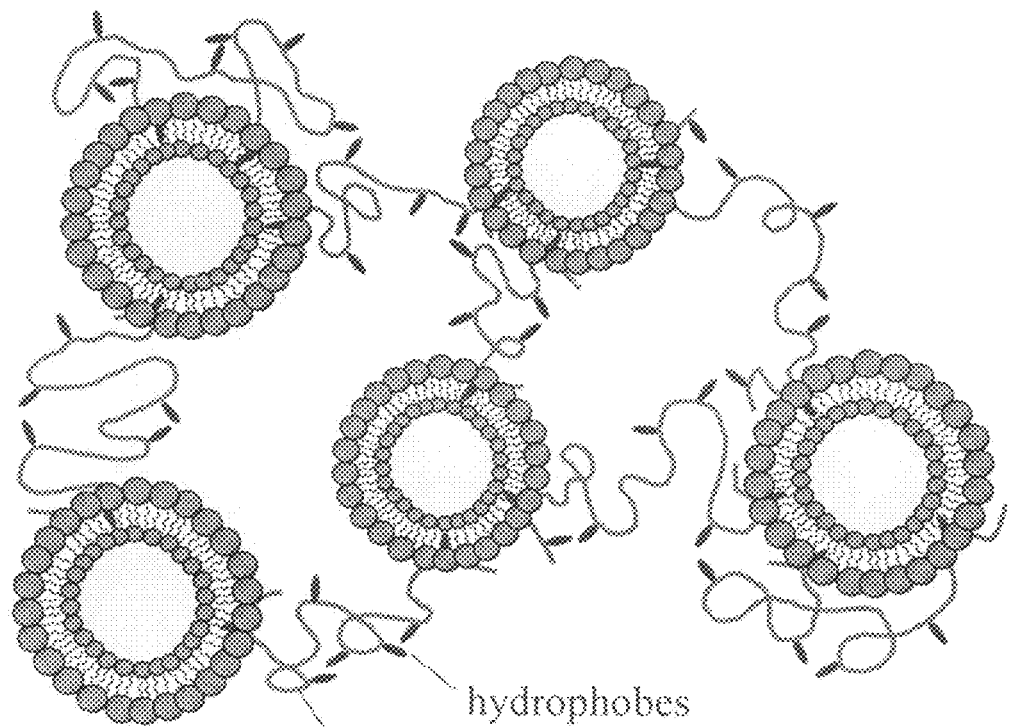
FIG. 3 is an illustration representing an hm-Chitosan film matrix wherein a plurality of liposomes (vesicle) cross-link the hm-Chitosan scaffolds.
Figure 4:
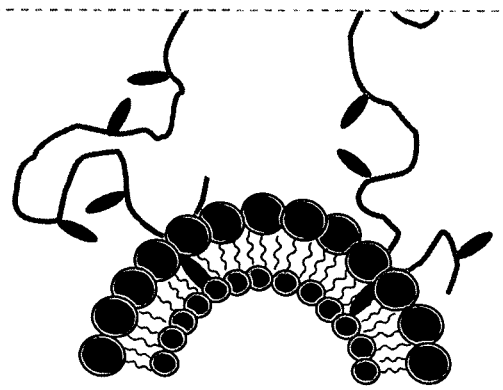
FIG. 4 is an illustration providing a representation of hydrophobic interaction between the hm-Chitosan and liposome (vesicle) bi-layer.
Figure 5:
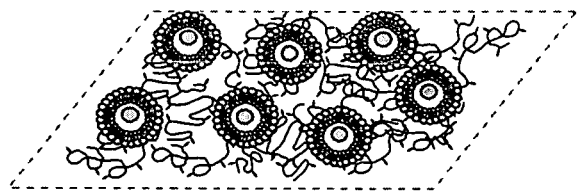
FIG. 5 is an illustration representing a solid-state functionalized film, including the hm-Chitosan bound with the vesicles based upon hydrophobic interaction of the hm-Chitosan scaffolds with the functionalized liposomes (vesicles), wherein the liposomes contain bioactive agents and/or moieties, and further illustrating the cross-linking of the numerous hm-Chitosan scaffolds by the liposomes.

In another preferred, alternative embodiment of a composition of matter for the current invention, an hm-Chitosan film matrix is bound with vesicles or liposomes through hydrophobic interactions. FIGS. 3, 4, and 5 provide exemplary, graphic illustrations representing a functionalized film of the current invention which includes the hm-Chitosan bound with the liposomes. Various exemplary, preferred embodiments of formation processes of the functionalized film are shown in FIG. 6 (PHASE II), 7, and 8. Similar to the solid-state, hm-Chitosan film matrix identified above, the functionalized networked film of the current invention is a solid-state, dry networked functionalized film. The formation processes, the cross-linking stabilizing effect that the vesicles or liposomes have on the matrix of numerous hm-Chitosan based films, and the "functionalization" or biological activity (e.g., pharmacological activity) of the vesicles or liposomes bound to the hm-Chitosan backbone may provide significant advantages to the current invention and such various component features are understood to fall within the scope of the current invention. In addition, FIG. 10 (described herein below) provides an exemplary graphical representation of the degradative release of the liposomes from the hm-Chitosan backbones, thus illustrating some of the in situ activity that is made possible by the current invention.

Figure 9:
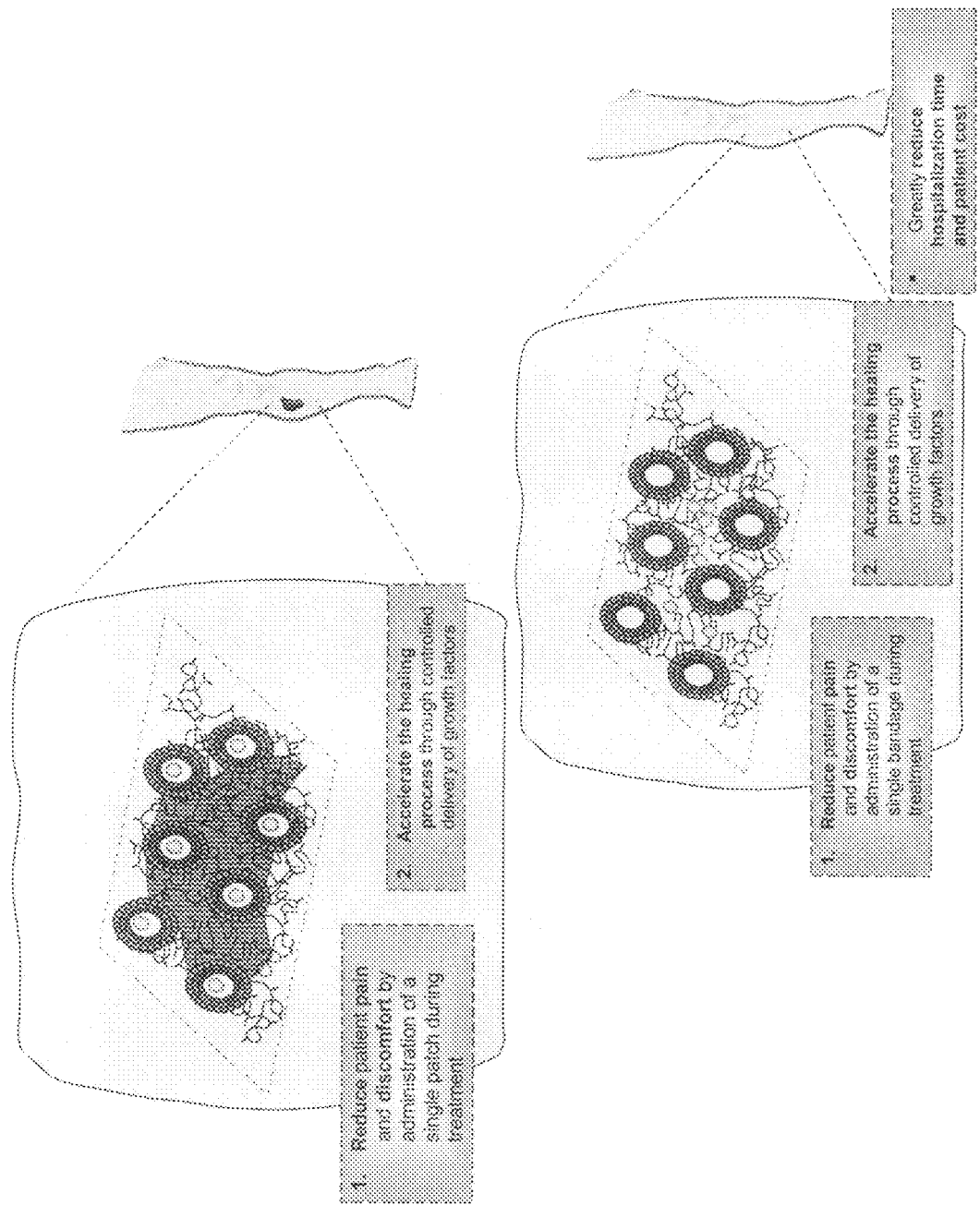
FIG. 9 provides an illustrative representation of an exemplary use of the functionalized film matrix of the current invention wherein an "injured" area has the solid-state, functionalized biopolymeric film matrix applied directly to the "injured" area, whereupon such direct application the active ingredients contained in the liposomes are released into the "injured" area to promote healing as shown in FIG. 10.
Figure 10:
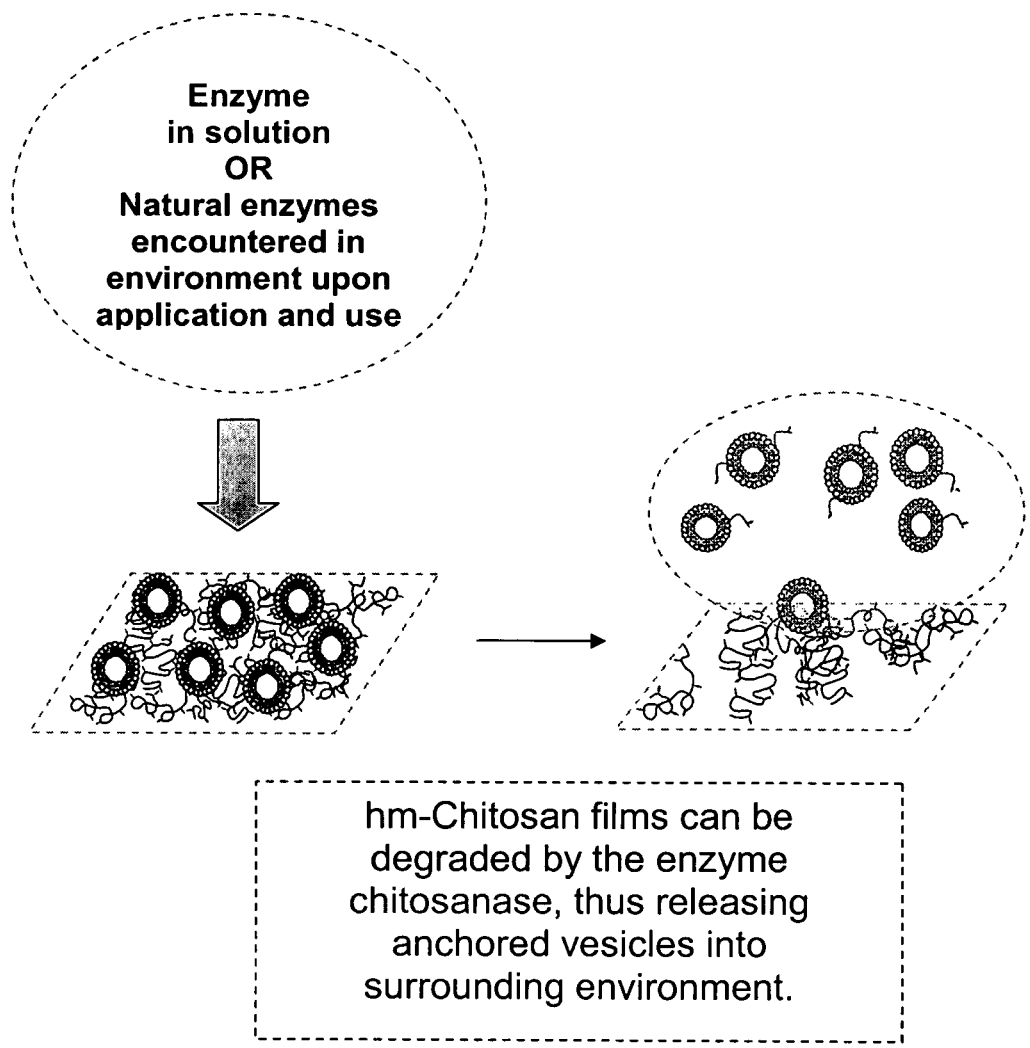
FIG. 10 is an illustration of the process of releasing the functionalized vesicles from the hm-Chitosan film matrices via enzymatic degradation in order to release the vesicles into an environment.
Figure 11:
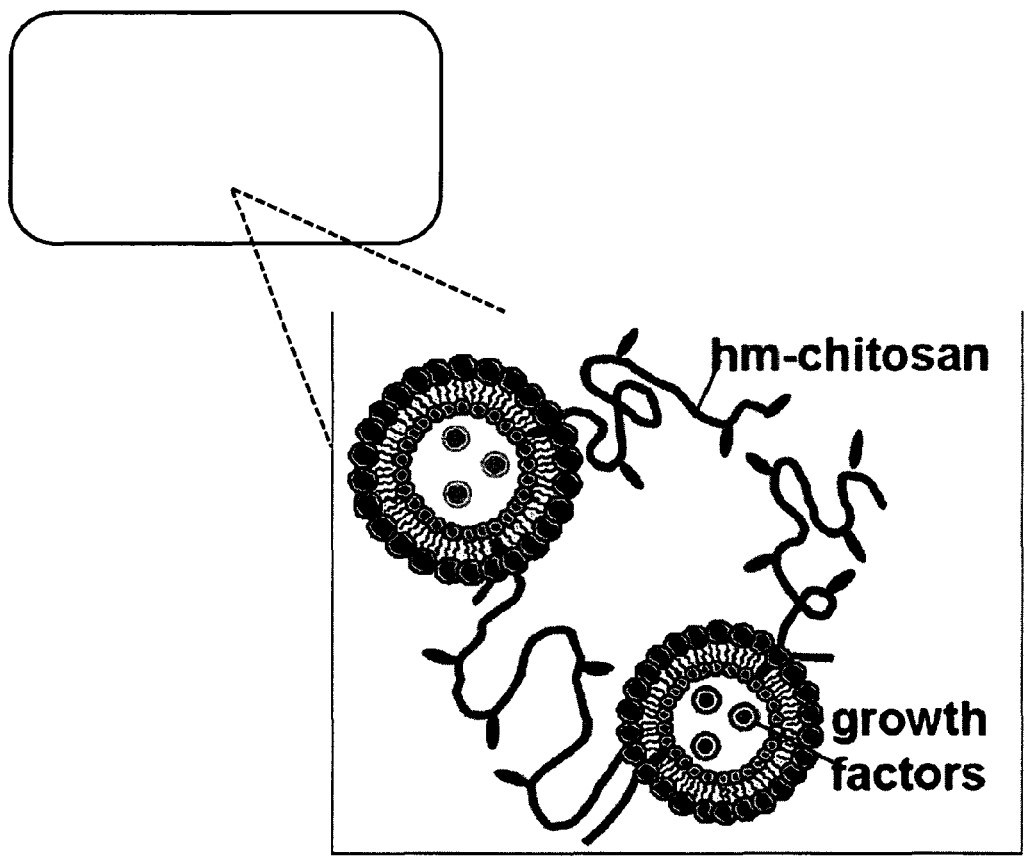
FIG. 11 is an illustration of another exemplary use of the functionalized film matrix of the current invention.

In alternative preferred embodiments, showing exemplary functional applications and uses of the functionalized film of the current invention, FIGS. 9 and 11 illustrate the current invention as it can be constructed and/or embodied within as a patch, bandage, and "wrap". As will be further described below herein, these illustrative representations of application and use of the current invention should not be read as limiting or exclusive and that those of skill in the art will understand that the embodiments within which the current invention may be employed may vary from encapsulated therapeutics, to various composition of matter formulations, to various "film" forms, to incorporation within various types of devices and/or mechanical forms, without departing from the scope and spirit of the current invention.

As used herein, functional group(s) (moiety or moieties) are specific groups of atoms attached to a carbon backbone of organic molecules that characterize the molecule and are responsible for the molecule's chemical reactivity such that the same functional group of atoms will generally undergo the same or similar chemical reactions(s) regardless of the size of the molecule it is a part of. The characteristics of chitosan and its derivatives typically give them an overall pKa value of ~6.5 and pH ~6, thus they are positively charged and soluble in acidic to neutral solution. Further, these types of reactive characteristics are often typical of strong bioadhesives, thus, chitosan and its derivatives may be readily able to bind to negatively charged surfaces, such as membranes (mucosal or otherwise), or molecules, such as various functional groups or moieties.

Generally, and in preferred embodiments of the current invention, the amino group or functional group for the chitosan backbone is where the positive charge of the molecule is "located". It is to be further understood that the chitosan scaffold may include numerous functional groups in various locations about its molecular structure. The amino functional group is typically where the amphiphilic compound will bind thereby presenting its hydrophobic tail to the outer environment and brining hydrophobic modification to the chitosan backbone. Due to the cyclic nature of the chitosan molecular structure the addition of the amphilic compound may generally occur via a process of nucleophilic addition. This is opposed to linear or "straight" chain hydrocarbons or aliphatic hydrocarbons, wherein the addition of molecules or compounds to the backbone is generally referred to as branching and the newly added organics as side-chains. It is to be understood that the general principles and characteristics of chemical bonding, such as those intra- and inter-molecular bonding forces that are applicable for such chemical and/or electromagnetic reactions and known to those skilled in the art, apply herein. Any description regarding or reference to chemical or electromagnetic bonding characteristics, such as anything related to orbitals, valency, charge dispersion (location), electronegativities, hydrophobic interactions, shall be understood to comply with the generally accepted wisdom in the field as known by those of ordinary skill in the art.

Figure 12:
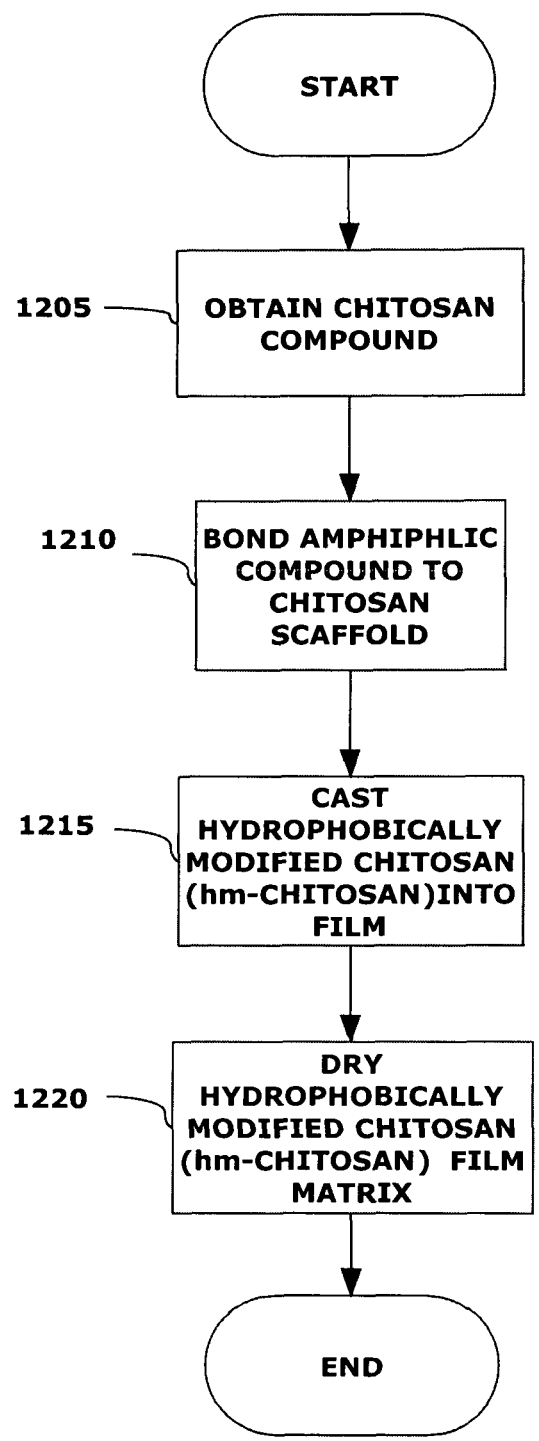
FIG. 12 is a graphical representation of a method of fabricating or forming a hm-Chitosan film matrix in accordance with an exemplary embodiment of the current invention.

In a preferred embodiment of the current invention, and from the PHASE I reaction process, as shown in FIG. 6, the chitosan backbone is hydrophobically modified by an amphiphilic compound. The amphiphilic compound, in a preferred embodiment, includes an aldehyde functional group associated with a saturated hydrocarbon. The formation process is graphically represented in FIG. 12, which illustrates a "Head") and a hydrophobic (hydrocarbon) group (the "Tail"). In the current embodiment, the basic formula for the aldehyde compound bound to the chitosan backbone is shown in the FIGS. 1A and 6 to be $C_{12}H_{25}$. Thus, the aldehyde functional group includes a hydrophilic, reactive C—O type (carbonyl group) bond at the Head and a hydrophobic, hydrocarbon Tail.

The binding of the amphiphilic compound with the chitosan scaffold occurs through a hydrophilic interaction, wherein the hydrophilic, aldehyde Head group interacts with the hydrophilic amino functional group of the chitosan scaffold. In a preferred embodiment, the reaction process between these two functional groups is a nucleophilic addition reaction process known as an alkylimino-de-oxo-bisubstitution organic reaction wherein a carbonyl compound interacts with an amine to form an imine, as follows:

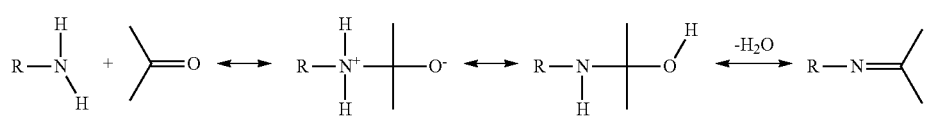

first step 1205 as obtaining chitosan compound or scaffold. This may be a solution containing numerous chitosan scaffolds that are readily reactive through their amine functional group. As shown, the chitosan may be formed or accomplished by the deacetylation of a chitin compound. After obtaining the chitosan compound of interest or a solution containing numerous such compounds, in step 1210, an amphiphilic compound is bound to the chitosan scaffold. In practical application, the amphiphilic compounds may be contained within a solution which is then mixed with the chitosan solution. The amphiphilic compounds bind through their functional groups, preferably the aldehyde functional group, with the amino functional group of the chitosan scaffolds. It is noted that typically ≤~10% of available amines will react and bond with the amphiphilic compounds. In preferred embodiments of the current invention, the percentage of amines that react and bond with the amphiphilic compounds is in the range of ~1.5% to 4.5%. This may be largely influenced by problems with solubility once the percentage of reacted amines goes over 5%. Once this binding has occurred the hydrophobically modified chitosan scaffold or backbone (hm-Chitosan) has been formed and now in step 1215 the hm-Chitosan is cast into film. In the final step 1220, the hm-Chitosan film is dehydrated or dried providing a novel solid-state, dry hm-Chitosan film matrix.

In current embodiments of the instant invention the amphiphilic compound is a $C_{12}$ aldehyde compound and it hydrophobically modifies the chitosan backbone through hydrophilic, covalent interaction with one of the available amino groups. This type of amphiphilic group may be commonly referred to as a short chain hydrophobe. It is understood that the $C_{12}$ aldehyde compound is an amphiphilic compound, having both a hydrophilic (carbonyl) group (the The imine may then be converted to a stable secondary amine by the addition of a mild reducing agent such as sodium cyanoborohydride ($NaBH_3(CN)$).

This is a two step reaction process that is acid catalyzed wherein the first step is an addition reaction forming an hemiaminal intermediate which transfers a proton from the nitrogen to the oxygen and then in the second step a dehydration or condensation reaction takes place and a water molecule is removed from the intermediate. Overall, the current invention proceeds to establish two new covalent bonds between the nitrogen of the amino group and the carbon of the carbonyl group. This reaction process promotes increased stability of the hm-Chitosan molecule as a lower energy state is reached as compared to a molecule where both amine and aldehyde functional groups are present.

In the current embodiment the association of the Head group with the amino group occurs through the formation of a new covalent bond, forming a strong double bond between the nitrogen atom of the amine and the carbon atom of the aldehyde. It is contemplated that other types of associations may be structured between the chitosan scaffold amino group and the aldehyde as may be desired, thus, the current exemplary embodiment should not be read as limiting or exclusive.

The amphiphilic compound, because of the C—O bond contained therein, is generally described and classified together with other types of functional groups that contain a carbon-oxygen bond (C—O). Further, it is known that the activity of the aldehyde functional group comes from the carbon atom double-bonded to an oxygen atom C═O, which is generally described and classified as a carbonyl group or carbonyl functional group. The carbonyl group classification is a characterization that applies to many different types of compounds, including the following:

| Carbonyl Compounds | Aldehyde | Ketone | Carboxylic acid | Ester |
|---|---|---|---|---|
| Structure | $\underset{R\phantom{xx}H}{\overset{O}{\underset{\|\|}{C}}}$ | $\underset{R\phantom{xx}R'}{\overset{O}{\underset{\|\|}{C}}}$ | $\underset{R\phantom{xx}OH}{\overset{O}{\underset{\|\|}{C}}}$ | $\underset{R\phantom{xx}OR'}{\overset{O}{\underset{\|\|}{C}}}$ |

| | | | | |
|---|---|---|---|---|
| General Forumla | RCHO | RCOR' | RCOOH | RCOOR' |
| Carbonyl Compounds | Amide | Enone | Acyl chloride | Acid anhydride |
| Structure | ![amide structure] | ![enone structure] | ![acyl chloride structure] | ![acid anhydride structure] |
| General Formula | RCONR'R" | RC(O)C(R')CR"R''' | RCOCL | (RCO)$_2$O |

It is contemplated that those of ordinary skill in the art may utilize alternative carbonyl functional groups as the hydrophilic Head group of an amphiphilic compound to react with the amino group of the chitosan backbone to provide the association of the amphiphilic compound with the chitosan backbone in a manner similar to that provided by the aldehyde compound. Thus, it is contemplated that the chitosan backbone may be hydrophobically modified through interaction with various, alternative organic compounds which may include alternative carbonyl functional groups.

In the current embodiment, the amphiphilic compound is described as further including a hydrocarbon Tail group associated with the reactive aldehyde (C=O) Head group. This hydrocarbon chain has a defining and useful characteristic in that it is hydrophobic in nature and therefore insoluble in water and capable of hydrophobic interaction. Hydrophobicity refers to a physical property of a molecule (i.e., hydrophobe) that is repelled from water because of its non-polar (no electric charge) nature. Thus, hydrophobes are "driven" together because they are unable to form polar (electrically charged) bonds with other molecules. For example, water molecules are electrically polarized and in a solution of hydrophobes and water, the water molecules will form hydrogen bonds with other water molecules and repel the nonpolarized hydrophobes. It is this repulsive, thermodynamic force and effect that is commonly referred to as the hydrophobic interaction, even though the energy is coming from the hydrophilic molecules.

The hydrophobic interaction is also a noncovalent type of chemical bond where the atoms and/or molecule(s) involved do not share pairs of electrons as the driving force of the bonding interaction, instead they use a more dispersed variation of electromagnetic interaction to hold the molecules or parts of molecules together, commonly referred to as a thermodynamic effect.

As described previously, the hydrocarbon chain is commonly referred to as a short chain hydrophobe. This generic reference is not intended to provide a particular limit on the length of the hydrophobic Tail group that may be employed with the current invention as any length hydrocarbon chain may fall within the scope and spirit of the current invention. It is to be understood that in the preferred embodiments of the invention the number of carbon atoms contained in the short chain hydrophobic Tail group of the amphiphilic compound may range from a minimum number of two (2) to a maximum number of fifty (50). In preferred embodiments of the current invention the number of carbon atoms in the hydrophobic Tail group may range from six (6) to thirty-six (36) and that more preferably the number of carbon atoms included in the hydrophobic Tail group is twelve (12). As will be described below, the number of carbon atoms, which define the length of the hydrophobic Tail group, may be dependent on the size of the hydrophobic cavity within the liposome (vesicle) bi-layer membrane.

Generally, the hydrophobic cavity is defined by the length of the hydrophobic chains extending from the hydrophilic heads of the lipids that form the bi-layer membrane. In the preferred embodiments, the hydrophobic chains of these lipids include eighteen (18) carbon atoms each. Therefore, the overall size (i.e., width) of the hydrophobic cavity is thirty-six carbon atoms long. Thus, it is generally preferred that the length (i.e., carbon backbone) of the hydrophobic Tail group of the amphiphilic compound that hydrophobically modifies the chitosan scaffold not exceed thirty-six (36) carbon atoms.

As used herein, hydrocarbon(s) are any organic molecule(s) or compound(s) with a "backbone" or "skeleton" consisting entirely of hydrogen and carbon atoms and which lack a functional group. Thus, these types of compounds are hydrophobic in nature, unable to react hydrophilically, and therefore provide an opportunity for hydrophobic interaction. The hydrophobic interaction capability of the amphiphilic compound bound to the chitosan backbone may provide significant advantage to the current invention when compared to the prior art in that the interaction of the hm-Chitosan with the liposomes or vesicles is a self-driven, thermodynamic process requiring less energy input. Thus, regardless of any particular form of the Tail group of the amphiphilic compound, so long as it provides the opportunity for hydrophobic interaction with the vesicles or liposomes it falls within the scope and spirit of the current invention.

Hydrocarbons, which are hydrophobic, may form into various types of compounds/molecules, such as gases (e.g. methane and propane), liquids (e.g., hexane and benzene), waxes or low melting solids (e.g., paraffin was and naphthalene), polymers (e.g., polyethylene, polypropylene and polystyrene), or biopolymers. Currently, hydrocarbons may be classified as follows:

1. Saturated Hydrocarbons (alkanes) are composed entirely of single bonds between the carbon and hydrogen atoms and are denoted by (assuming non-cyclic structures) the general formula $C_nH_{2n+2}$. These types of compounds are the most simple of the hydrocarbons and are either found as linear or branched species of unlimited number.
2. Unsaturated Hydrocarbons include one or more multiple bonds between carbon atoms of the compound, such as double bonds (alkenes-$C_nH_{2n}$) or triple bonds (alkynes-$C_nH_{2n-2}$). These multiple bonds create carbon atoms which are also commonly referred to as hydrogenated in that they are in need of the addition of further hydrogen atoms.

3. Cycloalkanes consist of only carbon and hydrogen atoms are cyclic or "ring-shaped" alkane hydrocarbons denoted by the general formula $C_nH_{2(n+-g)}$ where n=number of C atoms and g=number of rings in the molecule. Cycloalkanes are saturated because there are no multiple (double or triple) C—C bonds to hydrogenate (add more hydrogen to).

4. Aromatic Hydrocarbons, also known as arenes, are hydrocarbons that contain at least one aromatic ring and may be denoted by the formula $C_nH_n$, wherein at a minimum n=6. Arenes (e.g., Benzene-$C_6H_6$) or Aromatic Hydrocarbons include a molecular structure which incorporates one or more planar sets of six carbon atoms connected by delocalized electrons numbering the same as if they consisted of alternating single and double covalent bonds.

From this basic classification system there exist many derivatives and further types of compounds that build therefrom. For example, numerous and varied compounds include more than one aromatic ring and are generally referred to as polyaromatic hydrocarbons (PAH); they are also called polycyclic aromatic hydrocarbons and polynuclear aromatic hydrocarbons. Various alternative/derivative forms of the saturated or unsaturated cycloalkanes, and aromatic hydrocarbons as are known and contemplated by those skilled in the art may be employed with the current invention and should be read as falling within the contemplated scope of the current invention.

Various types of other hydrophobic, organic compounds may generally include hydrocarbon backbones but may also include other types of atoms and/or incorporate/bind to other compounds/molecular structures that incorporate other types of atoms than just carbon and hydrogen. Thus, another classification system has developed by which organic compounds with generally hydrocarbon backbones but bound with other types of molecules may be separated, wherein such compounds may be designated either aromatic or aliphatic. Thus, compounds composed mainly, substantially or at least partially, but not exclusively of carbon and hydrogen may be divided into two classes:

1. aromatic compounds, which contain benzene and other similar compounds, and 2. aliphatic compounds (G. aleiphar, fat, oil), which do not. In aliphatic compounds, carbon atoms can be joined together in straight chains, branched chains, or rings (in which case they are called alicyclic). They can be joined by single bonds (alkanes), double bonds (alkenes), or triple bonds (alkynes). Besides hydrogen, other elements can be bound to the carbon chain, the most common being oxygen, nitrogen, sulfur, and chlorine. Those of ordinary skill in the art will recognize that other molecules may also be bound to the carbon chains and that compounds of such heteroatomic structure are contemplated as falling within the scope of the current invention.

The hydrophobic Tail group of the amphiphilic compound bound to the chitosan backbone of the current invention is capable of branching and/or allowing the inclusion of side chains onto its carbon backbone. This may promote the hydrophobic interaction between the hm-Chitosan and liposomes, as will be discussed further below. It may be understood that the strength of the hydrophobic interaction is based upon the available amount of "hydrophobes" that may interact amongst themselves or one another. Thus, it may further promote the hydrophobic effect by increasing the amount of and/or "hydrophobic" nature of the hydrophobic Tail group that is interacting. For instance, a hydrophobic Tail group, which in its original form may include a hydrocarbon chain, may promote an increase in its hydrophobicity (ability to hydrophobically bond and strength of hydrophobic interaction) by having a hydrophobic side chain attach to one of the carbons of its carbon backbone. In a preferred embodiment of the current invention, this may include the attachment of various polycyclic compounds, which may include for instance various steroidal compounds and/or their derivatives such as sterol type compounds, more particularly cholesterol.

In alternative embodiments, the current invention contemplates the use of various molecules and/or compounds that may increase the hydrophobic interaction allowed between the Tail of the amphiphilic compound and the bi-layer membrane of the liposomes. The side chains may be linear chains, aromatic, aliphatic, cyclic, polycyclic, or any various other types of hydrophobic side chains as contemplated by those skilled in the art. Some of the contemplated hydrophobic side chains may include the following:

I. Linear Alkanes

| Number of C atoms | Formula | Common name | Synonyms |
|---|---|---|---|
| 1 | $CH_4$ | Methane | marsh gas; methyl hydride; natural gas |
| 2 | $C_2H_6$ | Ethane | dimethyl; ethyl hydride; methyl methane |
| 3 | $C_3H_8$ | Propane | dimethyl methane; propyl hydride |
| 4 | $C_4H_{10}$ | n-Butane | butyl hydride; methylethyl methane |
| 5 | $C_5H_{12}$ | n-Pentane | amyl hydride; Skellysolve A |
| 6 | $C_6H_{14}$ | n-Hexane | dipropyl; Gettysolve-B; hexyl hydride; Skellysolve B |
| 7 | $C_7H_{16}$ | n-Heptane | dipropyl methane; Gettysolve-C; heptyl hydride; Skellysolve C |
| 8 | $C_8H_{18}$ | n-Octane | dibutyl; octyl hydride |
| 9 | $C_9H_{20}$ | n-Nonane | nonyl hydride; Shellsol 140 |
| 10 | $C_{10}H_{22}$ | n-Decane | decyl hydride |
| 11 | $C_{11}H_{24}$ | n-Undecane | hendecane |
| 12 | $C_{12}H_{26}$ | n-Dodecane | adakane 12; bihexyl; dihexyl; duodecane |
| 13 | $C_{13}H_{28}$ | n-Tridecane | |
| 14 | $C_{14}H_{30}$ | n-Tetradecane | |
| 15 | $C_{15}H_{32}$ | n-Pentadecane | |
| 16 | $C_{16}H_{34}$ | n-Hexadecane | cetane |
| 17 | $C_{17}H_{36}$ | n-Heptadecane | |
| 18 | $C_{18}H_{38}$ | n-Octadecane | |
| 19 | $C_{19}H_{40}$ | n-Nonadecane | |
| 20 | $C_{20}H_{42}$ | n-Eicosane | didecyl |
| 21 | $C_{21}H_{44}$ | n-Heneicosane | |
| 22 | $C_{22}H_{46}$ | n-Docosane | |
| 23 | $C_{23}H_{48}$ | n-Tricosane | |
| 24 | $C_{24}H_{50}$ | n-Tetracosane | tetrakosane |
| 25 | $C_{25}H_{52}$ | n-Pentacosane | |
| 26 | $C_{26}H_{54}$ | n-Hexacosane | cerane; hexeikosane |
| 27 | $C_{27}H_{56}$ | n-Heptacosane | |
| 28 | $C_{28}H_{58}$ | n-Octacosane | |
| 29 | $C_{29}H_{60}$ | n-Nonacosane | |
| 30 | $C_{30}H_{62}$ | n-Triacontane | |
| 31 | $C_{31}H_{64}$ | n-Hentraiacontane | untriacontane |

-continued

| Number of C atoms | Formula | Common name | Synonyms |
|---|---|---|---|
| 32 | $C_{32}H_{66}$ | n-Dotriacontane | dicetyl |
| 33 | $C_{33}H_{68}$ | n-Tritriacontane | |
| 34 | $C_{34}H_{70}$ | n-Tetratriacontane | |
| 35 | $C_{35}H_{72}$ | n-Pentatriacontane | |
| 36 | $C_{36}H_{74}$ | n-Hexatriacontane | |
| 37 | $C_{37}H_{76}$ | n-Heptatriacontane | |
| 38 | $C_{38}H_{78}$ | n-Octatriacontane | |
| 39 | $C_{39}H_{80}$ | n-Nonatriacontane | |
| 40 | $C_{40}H_{82}$ | n-Tetracontane | |
| 41 | $C_{41}H_{84}$ | n-Hentetracontane | |
| 42 | $C_{42}H_{86}$ | n-Dotetracontane | |
| 43 | $C_{43}H_{88}$ | n-Tritetracontane | |
| 44 | $C_{44}H_{90}$ | n-Tetratetracontane | |
| 45 | $C_{45}H_{92}$ | n-Pentatetracontane | |
| 46 | $C_{46}H_{94}$ | n-Hexatetracontane | |
| 47 | $C_{47}H_{96}$ | n-Heptatetracontane | |
| 48 | $C_{48}H_{98}$ | n-Octatetracontane | |
| 49 | $C_{49}H_{100}$ | n-Nonatetracontane | |
| 50 | $C_{50}H_{102}$ | n-Pentacontane | |
| 51 | $C_{51}H_{104}$ | n-Henpentacontane | |
| 52 | $C_{52}H_{106}$ | n-Dopentacontane | |
| 53 | $C_{53}H_{108}$ | n-Tripentacontane | |
| 54 | $C_{54}H_{110}$ | n-Tetrapentacontane | |
| 55 | $C_{55}H_{112}$ | n-Pentapentacontane | |
| 56 | $C_{56}H_{114}$ | n-Hexapentacontane | |
| 57 | $C_{57}H_{116}$ | n-Heptapentacontane | |
| 58 | $C_{58}H_{118}$ | n-Octapentacontane | |
| 59 | $C_{59}H_{120}$ | n-Nonapentacontane | |
| 60 | $C_{60}H_{122}$ | n-Hexacontane | |
| 61 | $C_{61}H_{124}$ | n-Henhexacontane | |
| 62 | $C_{62}H_{126}$ | n-Dohexacontane | |
| 63 | $C_{63}H_{128}$ | n-Trihexacontane | |
| 64 | $C_{64}H_{130}$ | n-Tetrahexacontane | |
| 65 | $C_{65}H_{132}$ | n-Pentahexacontane | |
| 66 | $C_{66}H_{134}$ | n-Hexahexacontane | |
| 67 | $C_{67}H_{136}$ | n-Heptahexacontane | |
| 68 | $C_{68}H_{138}$ | n-Octahexacontane | |
| 69 | $C_{69}H_{140}$ | n-Nonahexacontane | |
| 70 | $C_{70}H_{142}$ | n-Heptacontane | |
| 71 | $C_{71}H_{144}$ | n-Henheptacontane | |
| 72 | $C_{72}H_{146}$ | n-Doheptacontane | |
| 73 | $C_{73}H_{148}$ | n-Triheptacontane | |
| 74 | $C_{74}H_{150}$ | n-Tetraheptacontane | |
| 75 | $C_{75}H_{152}$ | n-Pentaheptacontane | |
| 76 | $C_{76}H_{154}$ | n-Hexaheptacontane | |
| 77 | $C_{77}H_{156}$ | n-Heptaheptacontane | |
| 78 | $C_{78}H_{158}$ | n-Octaheptacontane | |
| 79 | $C_{79}H_{160}$ | n-Nonaheptacontane | |
| 80 | $C_{80}H_{162}$ | n-Octacontane | |
| 81 | $C_{81}H_{164}$ | n-Henoctacontane | |
| 82 | $C_{82}H_{166}$ | n-Dooctacontane | |
| 83 | $C_{83}H_{168}$ | n-Trioctacontane | |
| 84 | $C_{84}H_{170}$ | n-Tetraoctacontane | |
| 85 | $C_{85}H_{172}$ | n-Pentaoctacontane | |
| 86 | $C_{86}H_{174}$ | n-Hexaoctacontane | |
| 87 | $C_{87}H_{176}$ | n-Heptaoctacontane | |
| 88 | $C_{88}H_{178}$ | n-Octaoctacontane | |
| 89 | $C_{89}H_{180}$ | n-Nonaoctacontane | |
| 90 | $C_{90}H_{182}$ | n-Nonacontane | |
| 91 | $C_{91}H_{184}$ | n-Hennonacontane | |
| 92 | $C_{92}H_{186}$ | n-Dononacontane | |
| 93 | $C_{93}H_{188}$ | n-Trinonacontane | |
| 94 | $C_{94}H_{190}$ | n-Tetranonacontane | |
| 95 | $C_{95}H_{192}$ | n-Pentanonacontane | |
| 96 | $C_{96}H_{194}$ | n-Hexanonacontane | |
| 97 | $C_{97}H_{196}$ | n-Heptanonacontane | |
| 98 | $C_{98}H_{198}$ | n-Octanonacontane | |
| 99 | $C_{99}H_{200}$ | n-Nonanonacontane | |
| 100 | $C_{100}H_{202}$ | n-Hectane | |
| 101 | $C_{101}H_{204}$ | n-Henihectane | |
| 102 | $C_{102}H_{206}$ | n-Dohectane | |
| 103 | $C_{103}H_{208}$ | n-Trihectane | |
| 104 | $C_{104}H_{210}$ | n-Tetrahectane | |
| 105 | $C_{105}H_{212}$ | n-Pentahectane | |
| 106 | $C_{106}H_{214}$ | n-Hexahectane | |
| 107 | $C_{107}H_{216}$ | n-Heptahectane | |
| 108 | $C_{108}H_{218}$ | n-Octahectane | |
| 109 | $C_{109}H_{220}$ | n-Nonahectane | |
| 110 | $C_{110}H_{222}$ | n-Decahectane | |
| 111 | $C_{111}H_{224}$ | n-Undecahectane | |

II. Cyclic Compounds

Cyclic compounds can be categorized:

| | |
|---|---|
| Alicyclic Compound Cycloalkane Cycloalkene | An organic compound that is both aliphatic and cyclic with or without side chains attached. Typically include one or more all-carbon rings (may be saturated or unsaturated), but NO aromatic character. |
| Aromatic hydrocarbon Polycyclic aromatic hydrocarbon | See above and below |
| Heterocyclic compound | Organic compounds with a ring structure containing atoms in addition to carbon, such as nitrogen, oxygen, sulfur, chloride as part of the ring. May be simple aromatic rings or non-aromatic rings. Some examples are Pyridine (C5H5N), Pyrimidine (C4H4N2) and Dioxane (C4H8O2). |
| Macrocycle | See below. |

III. Polycyclic Compounds—polycyclic compound is a cyclic compound with more than one hydrocarbon loop or ring structures (Benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these. The following is a list of some known polycyclic compounds.

| Polycyclic Compounds | Sub-Types | Example Compounds |
|---|---|---|
| Bridged Compound -- compounds which contain interlocking rings | Bicyclo compound | adamantane amantadine biperiden memantine methenamine rimantadine |
| Macrocyclic Compounds -- any molecule containing a ring of seven, fifteen, or any arbitrarily large number of atoms | Calixarene Crown Compounds Cyclodextrins Cycloparaffins Ethers, cyclic Lactams, macrocyclic Macrolides Peptides, cyclic Tetrapyrroles Trichothecenes | |
| Polycyclic Hydrocarbons, Aromatic | Acenaphthenes Anthracenes Azulenes Benz(a)anthracenes Benzocycloheptenes Fluorenes Indenes Naphthalenes Phenalenes Phenanthrenes Pyrenes Spiro Compounds | |

-continued

| Polycyclic Compounds | Sub-Types | Example Compounds |
| --- | --- | --- |
| Steroids | Androstanes | |
| | Bile Acids and Salts | |
| | Bufanolides | |
| | Cardanolides | |
| | Cholanes | |
| | Choestanes | |
| | Cyclosteroids | |
| | Estranes | |
| | Gonanes | |
| | Homosteroids | |
| | Hydroxysteroids | |
| | Ketosteroids | |
| | Norsteroids | |
| | Prenanes | |
| | Secosteroids | |
| | Spirostans | |
| | Steroids, Brominated | |
| | Steroids, Chlorinated | |
| | Steroids, Fluorinated | |
| | Steroids, Heterocyclic | |

The addition of the side chains may increase the stability and strength of the hydrophobic interaction between the Tail group and hydrophobic cavity of the liposomes. This increase in strength and stability may provide further advantages in the ability of the hm-Chitosan film and functionalized film to self-assemble, such as providing increased or stabilized rates of reaction in the formation of the network film. The ability to adjust the side chain hydrophobicity may directly impact upon various characteristics of the complexed proteins contained within the films, such as the tertiary and quaternary structures of the hm-Chitosan backbone, either as a reactive, solid-state hm-Chitosan film matrix or as a networked, functionalized film including bound liposomes.

As is generally known, vesicles are relatively small membrane enclosed "sacs" that are able to store, transport, or digest cellular products and waste (various cellular substances) within an intracellular environment. While the overall size of these "sacs" may vary it is known that they may range from nano-scale sizes to larger sizes. Two standard types of vesicles may be distinguished by their membrane layer. Where the enclosed "sacs" of the vesicles are separated from an exterior environment, such as a cytosolic environment, by a membrane composed of a hydrophilic "head" region in contact with the surrounding environment and sequestering the hydrophobic "tail" regions in the center, they are commonly referred to as micelles. Where the membrane of the vesicle is composed of at least one lipid bilayer (unilamellar vesicles) that encloses or forms about an interior cavity or intravesicular environment they are typically referred to as liposomes. While it is common that the intraliposomal (intravesicular) environment be a hydrophilic one, alternative environments may be found or created within these interior cavities of the vesicle or liposome.

Generally, the liposomes otherwise known as phospholipid vesicles, are biocompatible nano-scale structures which have been shown to have numerous applications as will be discussed. The liposomes are generally spheroid structures and typically contain a hydrophilic (water-filled) core or interliposomal cavity that is capable of storing and/or transporting water soluble substances within and an oily (hydrophobic) shell made up of hydrophobic (water-fearing or repelling) substances which may store and/or transport hydrophobically soluble compounds which may include various bioactive agents or moieties and/or may include various biomarkers for detection, as will be discussed. The various types of agents, moieties, markers and/or otherwise may be included within the membrane bi-layer and may interact across one or more of the bi-layers without departing from the scope and spirit of the present invention. The hydrophobic cavity exists between the "head" groups of the surfactant molecules that form the bi-layer membrane of the liposome. The size of these cavities may also vary from nano-scale to larger sizes.

Vesicles and particularly liposome structures have been of particular interest because of their ability to entrap desired chemicals in their interior and thereafter release these chemicals to the external environment in a controlled manner. Some of the various types of substances contained within the various cavities have been known to provide functional components that may range in operation and application from therapeutics (pharmaceuticals/biologics/medicines), to drug delivery and controlled release, to bioseparations and sensing, to cosmetics, to herbicides, pesticides or other agricultural applications, to nutraceutical, to pain relief, to various structural applications. The size of these constructed compounds may also vary from nano-scale to larger than nano-scale sizes and be contained within the cavities vesicle or liposome.

The functionality of the chitosan scaffold may be significantly enhanced by first packaging various bioactive agents/reactive agents into the vesicles (liposomes), and subsequently anchoring them to the chitosan scaffold. Generally, and as will be described as the formation processes herein below, this enhanced functionality may be achieved by either passing a solution of vesicles over a dry chitosan film, or by detaching the chitosan scaffold from a surface substrate and subsequently dipping it into a vesicle solution. The resulting functionalized biopolymeric networked film or functionalized film, may be capable of such activity as delivering drugs or bioactive proteins, such as platelet-derived growth factor (PDGF), epidermal growth factor (EGF) and basic fibroblast growth factor (bFGF) to significantly accelerate the regeneration of damaged tissue, as well as vascular endothelial growth factor (VEGF) to promote growth of new blood vessels within the new tissue. Furthermore, by tailoring vesicle (liposome) composition, the release time and dose of drugs, proteins or other bioactive agents administered to the wounds or other appropriate environments can be controlled. In addition, since chitosan is an amino polysaccharide, different chemicals (e.g., anchoring molecules, such as the RGD peptides) can be chemically attached to the scaffold. Again, it is this "readily reactive" characteristic of chitosan that is often lacking in other biopolymers and allows the current invention to be tailored to address the needs of various, numerous, and particular types of applications.

As previously identified, liposomes are generally, spherical vesicles with at least one lipid bilayer membrane typically composed of phospholipids (lipids containing phosphate) and cholesterol (steroidal derivative polymer). It is common for liposome composition to include naturally-derived phospholipids with mixed lipid chains or pure surfactant components like dioleoylphosphatidylethanolamine (DOPE). Surfactants are amphiphilic (hydrophilic and hydrophobic) compounds or wetting agents that lower the surface tension of a liquid or the interfacial tension between two liquids. Thus, the bilayer membrane(s) of liposomes (vesicles) are composed of surfactant (amphiphilic) compounds that form about or around the intraliposomal environment (aqueous, hydrophilic, or otherwise) contained and enclosed within the liposome.

As previously mentioned, it is known to have multi-layered liposomes (vesicles) which are actually liposomes within liposomes or vesicles.

(See, Jae-Ho Lee, Vivek Agarwal, Arijit Bose, Gregory F. Payne, and Srinivasa R. Raghavan, *Transition from Unilamellar to Bilamellar Vesicles Indusced by an Amphiphilic Biopolymer*, APS, Physical Review Letters 2006, 96, 048102-1-4, which is herein incorporated by reference in its entirety.)

These multilamellar structures may be of various sizes and numbers of structural components and may include no or various biologically/pharmacologically active agents, ingredients, moieties, reactive elements, and the like as contemplated by those skilled in the art. These bioactive agents typically come in the form of functional groups or moieties, as discussed previously. For instance, the overall size of the liposome as defined by the outer bi-layer may range from below to above 100 nanometers while one or more secondary liposomal structures such as an inner bi-layer, which may be contained within the outer bi-layer of the liposomal structure, may range from below to above 100 nanometers. Multilamellar structures may include one or more secondary liposomal structure(s) or inner bi-layers contained within the outer bi-layer liposomal structure.

The bioactive agents contained within either or both the outer bi-layer and/or inner bi-layer may be homologous or heterologous with one another and capable of providing various desired functional characteristics. The scope of the bioactive capabilities of the liposomal or vesicular structures is only limited by the needs of the creator of the structure. Thus, the current invention may find practical application across various technology, industrial, medicinal, cosmetic, agricultural and other fields as have been identified and those other fields that may be contemplated by those of ordinary skill in various fields of art.

As discussed and shown throughout the drawing figures, the liposomes of the preferred embodiments of the current invention are attached to the hm-Chitosan film matrix through hydrophobic interaction. As shown in FIGS. 3 and 4, the hydrophobic interaction between the hm-Chitosan and the liposomes occurs via the "insertion and anchoring" of the hydrophobic Tail group of the amphiphilic compound into the lipid (i.e., phospholipid) bi-layer membrane of the liposome. The insertion process is driven by the generally understood hydrophobic interaction and those forces that are at work which tend to group like molecules when they exist in a heterogenous environment. Thus, the hydrophobic effect or interaction is evidenced by the tendency of hydrophobic components to group together versus interacting or bonding with other molecules.

The anchoring of the hydrophobic molecules is also a result of the hydrophobic interaction and these hydrophobic molecules will tend to stay grouped together as they form multiple bonds between different parts of the same molecule or between different molecules. Using these hydrophobic interactions the liposomes are anchored to the hm-Chitosan matrix by means of self-assembly. The self-assembly method for formation of the current invention's biopolymeric networked film is a thermodynamically driven process requiring little energy to drive the reaction/bonding process and resulting in complexed molecules with reduced energy states.

The liposomes, as shown in FIG. 3 and as may be seen throughout the other drawing figures of the instant application, act as physical cross-links between the numerous hm-Chitosan scaffolds within the biopolymeric networked film. As used herein, "cross-links", "cross-linkers" or "cross-linking" are descriptive of the use of molecules to form bonds that link one polymer chain to another and are typically employed to promote a difference in the polymer's physical properties. Numerous and varied cross-linkers are typically used to analyze subunit structure of proteins, protein interactions, and various parameters of protein function.

In a preferred embodiment of the current invention, the employing of liposomes or vesicle structures for cross-linking the hm-Chitosan scaffolds provided the 3-dimensional network from which the biomaterial compositions of matter, specifically the solid-state, dry hm-Chitosan and functionalized films of the current invention were formed. (See, Jae-Ho Lee, John P. Gustin, Tianhong Chen, Gregory F. Payne, and Srinivasa R. Raghavan, *Vesicle-Biopolymer Gels: Networks of Surfactant Vesicles Connected by Associating Biopolymers*, ACS, Langmuir 2005, 21, 26-33; and Chao Zhu, Jae-Ho Lee, Srinivasa R. Raghavan, and Gregory F. Payne, *Bioinspired Vesicle Restraint and Mobilization Using a Biopolymer Scaffold*, ACS, Langmuir 2006, 22, 2951-2955, both publications are herein incorporated by reference in their entireties.)

As stated previously, the Liposomes may be loaded with various bioactive/chemically reactive agents. When the liposomes are so formed they may be commonly referred to as "functionalized" and thus, when these functionalized liposomes are attached, via hydrophobic interaction(s), to the novel, solid-state hm-Chitosan film matrix then a preferred embodiment of the current invention is a functionalized biopolymeric networked film or functionalized film, as stated previously.

A preferred embodiment of a formation process of the functionalized film of the current invention is shown in FIG. 6 (PHASE II). In this process the novel, solid-state, dry hm-Chitosan film matrix is interacted with a vesicle solution which is dropped onto the film and allowed to soak for a specified period of time. That period of time may range from seconds, to minutes, to hours, to days, depending on the reaction conditions, composition of the vesicle (liposome) solution, condition of the hm-Chitosan film, and various other factors as contemplated by those skilled in the art. After soaking has been allowed for the specified period of time, the film is rinsed off with a buffer solution to remove any excess and unbound liposomes. The binding of the vesicles is via the hydrophobic interaction and the bonds that are formed are non-covalent. This is a significant advantage over the prior art, which typically "mixed" the vesicle and polymer and did not utilize hydrophobic interactions as is used by the current invention, in that the non-covalent bonds are formed through a self-assembly process that is thermodynamically driven and therefore requires less energy and promotes the formation of more stable, lower energy states for the complexed molecules.

Figure 13:
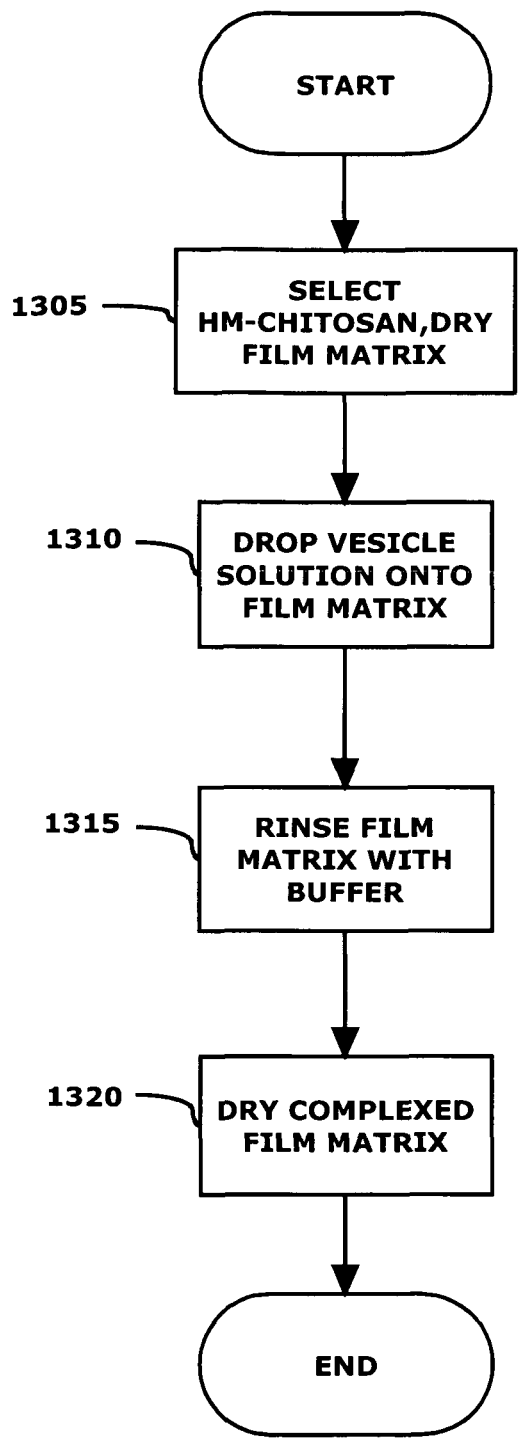
FIG. 13 is a graphical representation of a method of fabricating or forming a functionalized film in accordance with an exemplary embodiment of the current invention.
Figure 14:
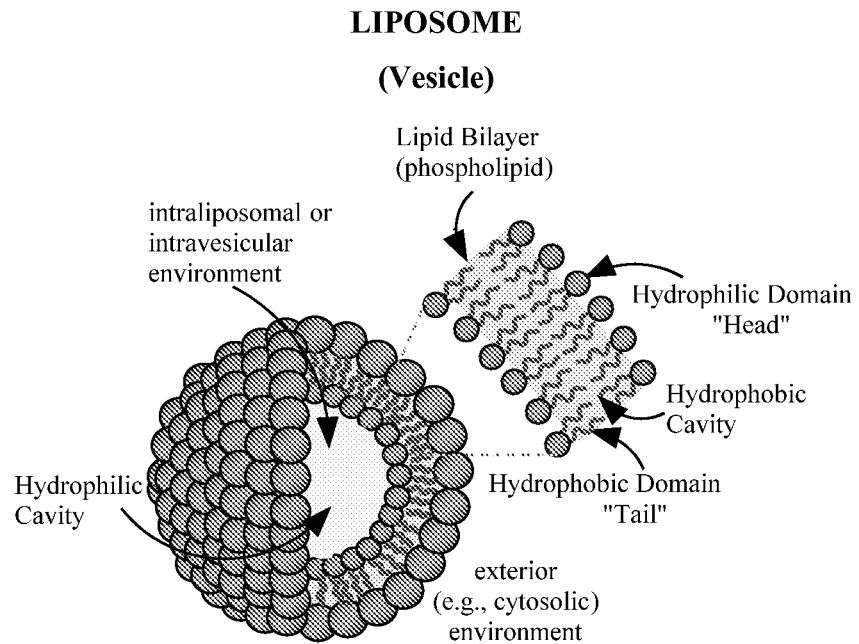
FIG. 14 is a diagram of a liposome.
Figure 15:
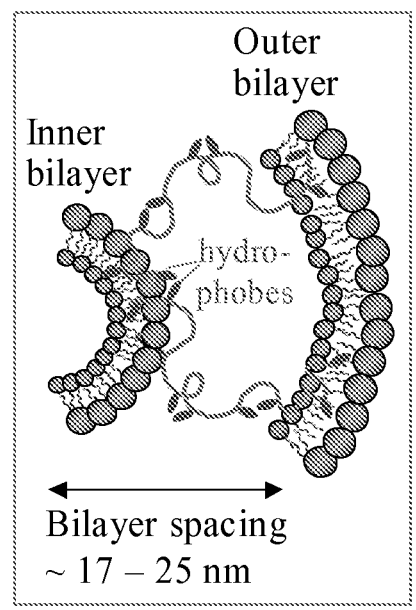
FIG. 15 is a diagram of a lipid bilayer in a liposome.

A novel method for formation or fabrication of the functionalized film of the current invention is shown in FIG. 13. In this formation process the first step 1305 is to select or obtain a solid-state, dried hm-Chitosan film matrix in accordance with the composition of matter described previously in the instant specification. Then in step 1310, a vesicle solution is dropped onto the film. The process may also include a step of specifying a period of time for which the vesicle solution may be allowed to soak onto the hm-Chitosan film matrix. Then in step 1315, the soaking vesicle solution is rinsed off the hm-Chitosan film matrix using some type of buffer solution. Upon completion of the rinsing step, step 1320 is a dehydrating process, wherein the complexed, film including liposomes bound to the hm-Chitosan scaffold matrix is allowed to dry. The final composition of matter obtained from this process is a solid-state, dry functionalized film.

By way of example and without intending to limit the scope and spirit of the present invention, the following are two alternative, exemplary approaches to the fabrication of the current invention. In the first fabrication process, the first step is to dissolve hydrophobically-modified chitosan in an aqueous acidic solution such as 0.2 M acetic acid, lactic acid or formic acid. Optimal concentrations of hm-chitosan in these initial solutions are 0.5 to 1.5 (w/v) %. Once the hm-chitosan is completely dissolved in solution, the resulting liquid is cast into a film by pouring it onto a glass plate followed by drying in a vacuum oven for 48 h at 37° C. After drying, the film can be peeled off the glass surface and stored in an air-tight container at ambient conditions for further and/or later use.

Another method of drying the liquid hm-chitosan solution is lyophilization. In this case the liquid cast onto the glass plate can be frozen by placing it at −20° C. for 2 hours. The resulting frozen film can be placed in a freeze-drying chamber under high vacuum for 24 hours. Once all solvent is removed from the biopolymer, the 'sponge-like' film can again be carefully peeled off of the glass and stored for further use.

The difference between the two methods of drying as it relates to the film properties is that the biopolymer chains have much less space between each other after drying in a vacuum oven. In the case of lyophilized films, the biopolymer chains cannot rearrange themselves as water molecules are being removed from the system. Hence the lyophilized films have a much higher degree of flexibility, but yet a significantly lower degree of tensile strength as compared to the vacuum-oven-dried films. Also, the vacuum-oven-dried films are transparent, whereas the lyophilized films are opaque.

Figure 7:
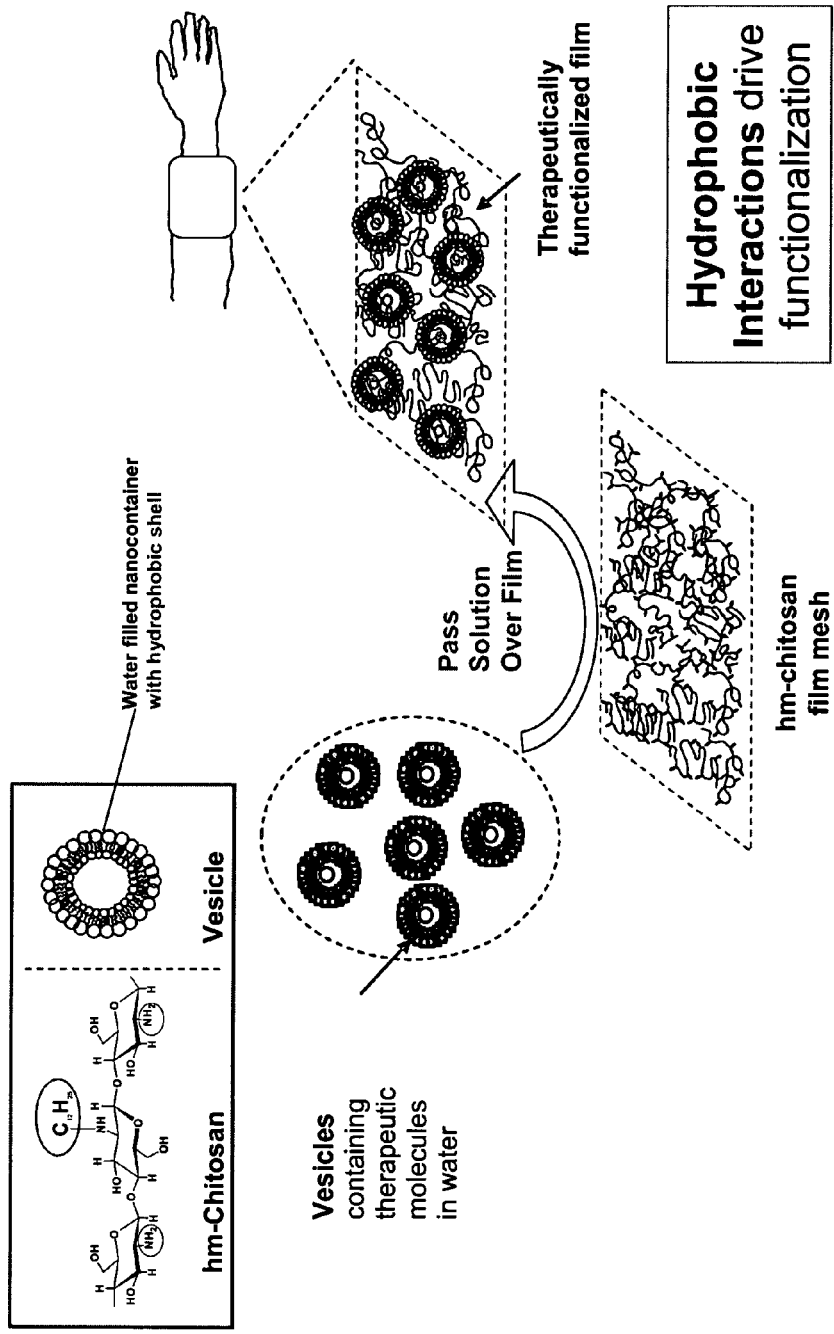
FIG. 7 is an illustration of another exemplary process of forming a functionalized film matrix, wherein the solid-state, dry film matrix of hm-chitosan has functionalized liposomes introduced to it, wherein the liposome may include nothing or various moieties or therapeutics or other biologically (pharmacologically) active agents, and through hydrophobic interactions form a complex that provides the functionalized film matrix is formed.
Figure 8:
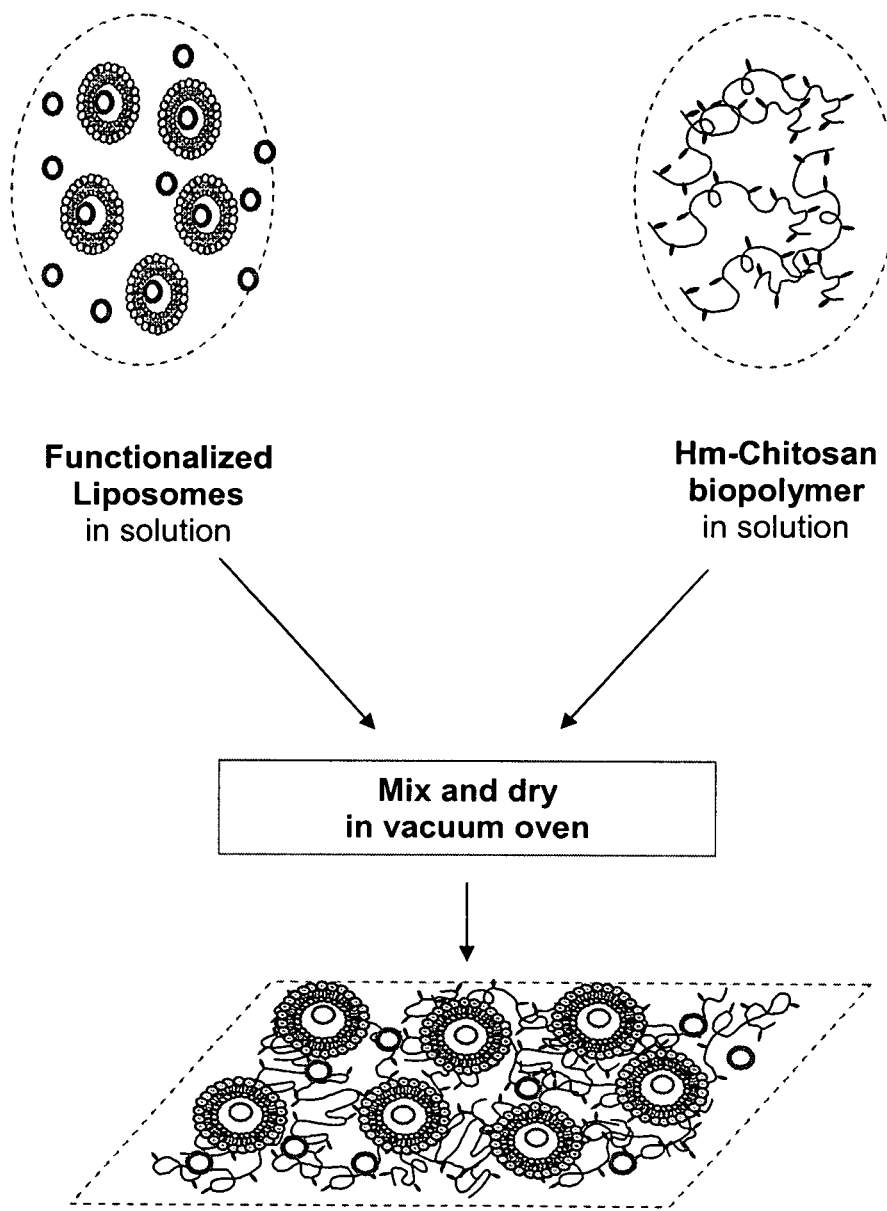
FIG. 8 is an illustration of another exemplary process of forming a functionalized film matrix in accordance with an exemplary embodiment of the current invention.

As shown in FIGS. 7 and 8 differences in the processes through which the vesicle or liposomes are interacted with the hm-Chitosan film matrix are contemplated. FIG. 7 shows that the vesicle solution is passed over the hm-Chitosan film and allowed to dry, without the rinsing with a buffer step. FIG. 8 shows that the process can be achieved with both the vesicle/liposomes and hm-Chitosan components in a solution state which is then mixed and dried to form the functionalized film. As previously stated, in a further alternative, preferred embodiment, the chitosan scaffold may be detached from the surface substrate upon which it was cast (e.g., glass) to form the film and then it may be subsequently dipped or immersed into a vesicle solution. The length of time or number of times this "dipping" or "immersion" process occurs may be varied as contemplated by those of skill in the art.

A practical application of the current functionalized film, as shown in FIGS. 7 and 11, and as represented in FIG. 9, is in the arena of wound dressings for the healing of wounds, chronic or otherwise. Each year 71 million people around the world physically experience the pain and horror of hospitalization due to serious wound or burn injuries. The 39 million suffering from chronic wounds (e.g. diabetic ulcers, venous ulcers and pressure sores) and burns unfortunately must also bear the financial strain of an estimated $3000-$5000 per day in inpatient care during recovery periods of up to 20 weeks. The guiding vision for this project stems from the motivation to vastly improve the lives of such chronic wound and burn patients, both in their medical treatment and in their finances. Conventional treatments of patients with non-healing wounds include extended stays within hyperbaric oxygen chambers as well as daily cleaning and disinfection of the damaged tissue between wound dressing changes. Biomedical engineers seeking to improve this dismal regimen of therapy have exploited the crucial role of growth factors in accelerating wound healing; this has already led to the development and regulatory approval of one topically applied platelet-derived growth factor (PDGF), the active component of the commercially available Regranex™ Gel. Although this gel represents an advancement in wound treatment, it has not achieved clinical results that outpace its cost (~$300 per daily dose). Also, Regranex™ Gel does not inherently prevent infection, nor does it control moisture and oxygen transfer to the wound, both of which are essential for proper wound healing.

The currently and commonly available wound dressings may be categorized into two major groups: (1) chitosan dressings (Hemcon, Chitoskin) and (2) all other dressings including foam, film, hydrocolloid and alginate dressings (C are Pro, Inc., Brennan and Integra Lifesciences, Corp.). The advantages of chitosan use as wound dressing are that chitosan and its derivatives have been found to promote fibroblast growth and affect macrophage activity, both of which accelerate the wound healing process; Chitosan derivatives also exhibit good homeostatic properties as well as broad spectrum antimicrobial capabilities, for example, chitosan acetate has been shown to be superior to both currently available alginate bandages and silver sulfadiazine in killoing bacterial. As a result, a commercial wound dressing product made of chitosan (The HemCon® Bandage) appeared in the market in 2004 and is currently employed in treating wounds suffered by American soldiers in both Iraq and Afghanistan.

However, both types of wound dressing have their limited abilities to cover multiple types of wounds or different stages of treatment. For example, currently all HemCon products are for the sole purpose of stopping hemorrhage. The usefulness of such products is limited to the first stage of severe wound treatment and is not favorable for use on burn injuries. In the preferred embodiments of the current invention, which incorporates the enhanced functionality and controlled release, the functionalized biopolymeric networked film may promote increased healing performance during the initial stages of wound and burn injury but also may provide increased wound healing performance during the later and more critical stages of recovery, such as tissue regeneration. Also, the current invention may promote significantly more useful treatment of wounds in patients with compromised healing ability, such as is found with the elderly, the very young, and diabetics.

Therefore, a continued need exists for multi-functional biomaterials that are able to accelerate the healing of damaged tissue, prevent microbial infection, and maintain adequate transfer of oxygen and moisture, all while keeping treatment costs at a commercially feasible level. In a preferred embodiment of the current invention, the functionalized film is incorporated into bandages for chronic wound and burn patients that aim to fill these largely unmet clinical needs. The functionalized film has packaged protein growth factors into lipid nano-containers ("liposomes") and subsequently anchored these containers to the biopolymeric film matrix by means of a self-assembly process. The beauty of the self-assembly method for fabrication is that the process is thermodynamically driven. The resulting bandage may promote the ease with which various bioactive proteins are incorporated and delivered to damaged tissue at a controlled and biologically relevant rate. The novel functionalized film of the current invention, the formation of which is driven by hydrophobic interactions, may assist in providing several advantages over traditional products due to one or more of the following noted characteristic features of the functionalized film: 1) incorporation of multiple healing functions within one device; 2) optimization of the healing process by providing a platform from which to deliver a wide range of therapeutic agents at a specific rate dictated by specific patient needs; 3) freedom from costly requirements for sophisticated device production techniques; 4) packaging of protein therapeutics within liposomal nano-containers, which allows for retention of molecular bioactivity during storage; 5) usage of the device matrix material, chitosan, a cheap and biocompatible material that demonstrates optimal characteristics for wound healing due to its excellent hemostatic (ability to stop bleeding) and anti-microbial properties.

The acceleration of chronic wound healing by sustained release of growth factors into wounded tissue has been studied for over 20 years, but is still not thoroughly understood. When growth factors are delivered as a bolus (e.g. administration of Regranex™ Gel), rapid clearance from the wound site occurs, making it difficult to maintain therapeutic concentrations over prolonged periods of time. Bolus administration thus necessitates large amounts of growth factors that may have dangerous side effects, such as vascularization of non-target tissues. For growth factors to promote wound healing, they should therefore be delivered in a sustained manner. The use of a sustained release vehicle, such as the novel polymer matrix of the current invention, to deliver the growth factors ensures an increased cell response while minimizing the total dose required.

In addition to the release kinetics, the stability of growth factors is equally crucial for eliciting cell responses. Polymer matrices have been widely used as depots for sustained drug delivery. However, in contrast to synthetic, low molecular weight drugs, proteins have limited chemical and physical stability which becomes evident in their susceptibility to proteolysis, chemical modification and denaturation, even within a polymer matrix environment. The solution provided by the current invention to the stability issue is "encapsulation" within liposomes. The attractiveness of liposomes as protein delivery systems can be assigned to the fact that the encapsulated proteins may remain in their preferred aqueous environment within the vesicles while the liposomal membrane protects them against proteolysis and other destabilizing factors. However, the liposomes themselves are unstable in biological environments and are rapidly uptaken by macrophages of the reticuloendothelial system in vivo.

The value of combining the advantages of polymers and liposomes for wound healing by embedding protein-containing liposomes within a fibrin mesh has been previously validated by various studies. In one particular study, the release rate of the protein (horseradish peroxidase, HRP) was entirely dictated by the degradation rate of the fibrin, and the activity of the HRP was largely retained upon release. However, these studies have not addressed the novel compositions of matter, systems, kits and fabrication processes, utilized by the current invention which is employing a novel liposome-embedded polymer matrix, wherein in the preferred embodiments, the matrix consists of a inexpensive biodegradable material, chitosan. By mixing a hydrophobically-modified (hm)-chitosan ($C_{12}$-hydrophobes covalently attached to the hydrophilic backbone) in solution with liposomes and then casting it into a film, an elastic composition of matter or medical device is formed by the current invention. FIGS. 7 and 11 illustrate such a flexible, elastic wound healing medical device.

In a preferred embodiment, the film results from mixing solutions of 0.5 wt % hm-chitosan and 1.2 wt % liposomes and then drying the complexed solution in a vacuum. It is known that individual solutions of hm-chitosan and liposomes at the same respective concentrations are both thin fluids of low viscosity. However, their mixture forms an elastic composition of matter due to the insertion of hydrophobes from the polymer backbone into the hydrophobic bilayers of the liposomes, resulting in a 3-dimensional network in which the liposomes act as physical cross-links.

The current invention, utilizes this novel, solid-state hm-Chitosan film, which has physical attributes suitable for dressing a wound (flexibility, adhesiveness, transparency for monitoring). Then via fabrication steps and processes, the film has growth factor-containing liposomes attached, for example, simply by soaking the film in a solution of liposomes. FIG. 7 shows a schematic of the fabrication process for creating such an hm-chitosan/liposome wound dressing by self-assembly. Note that the anchoring of liposomes occurs simply by hydrophobic, non-covalent interactions between the hydrophobes and the liposomal bi-layers.

The hm-Chitosan film anchors liposomes by means of simple, non-covalent interactions. Results of the novel films capabilities with regards to anchoring liposomes are shown below in Schematic 1. The novel functionalized film material was made simply by soaking an hm-Chitosan film in a solution of fluorescently-tagged liposomes at physiological pH. The fluorescence microscopy images clearly show bright fluorescence from the hm-Chitosan film, indicating that a large number of liposomes are anchored. In comparison, liposome anchoring (and thereby, fluorescence) is negligible for the unmodified chitosan controls. Also, this spontaneous anchoring of the liposomes onto hm-Chitosan may be a time-dependent process, as the fluorescence intensity appears to have increased significantly during the 20 minute interval. Thus, these results demonstrate that hm-chitosan films can be therapeutically functionalized with liposomes for biomedical applications. The ease of this fabrication process may provide cost and time advantages and it should be readily apparent to those skilled in the art that this novel formation process allows the current invention to be utilized in a broad range of fields of application.

Schematic 1. Anchoring of vesicles to hm-chitosan films demonstrated by fluorescence microscopy (bright red color). In comparison, the control chitosan films show negligible vesicle adherence.

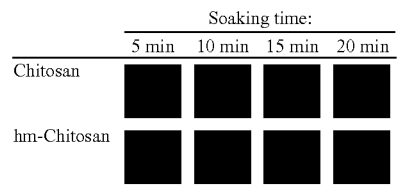

In an alternative, preferred embodiment of the current invention, a functionalized film is employed as part of an implantable material or is formulated for drug delivery. The scaffolds are biocompatible and biodegradable, thus, they may be loaded with drugs either inside the bulk matrix or within the liposomes themselves. This may allow for the possibility of having two or more drugs, or other bioactive agents, loaded within the device employing the functional film, and the device may have two or more distinct sets of release kinetics as a result. Also, the matrix of the functionalized film will swell upon the transition from physiological pH 7.4, to lower pH values of 6 or below, as often observed in cancerous tissue. Therefore, the matrix may act as a "smart" biomaterial which may promote the release drug(s) or other bioactive agent(s) with increased speed or expediency in response to a drop in pH. Capsules may be formed from the film through various processes known to those skilled in the art and/or by dropping a mixture of liposomes and hm-Chitosan into a solution of negatively charged surfactant or biopolymer. These container-within-container structures may similarly be used as multiple drug/bioactive agent release devices in addition to providing targeted release by conjugating moieties such as antibodies or RGD peptides to the surface of the capsule. The types of antibodies or other "ligand" structures that may be conjugated with the current invention may vary as contemplated by those of skill in the art, wherein the conjugative process is commonly known and easily performed, such that the reactivity of the free amine groups which are present on the capsule surface may be utilized.

The delivery mechanisms employed by the current invention may vary significantly. Delivery of the functionalized biopolymer may preferably occur through ingestion, formulated as a capsule. It is contemplated that the functionalized biopolymer compound may be formulated as an aqueous solution, such as a liquid drink, and allow for oral ingestion. Further, the functionalized biopolymer compound may be formulated as an organic compound including all solid oral formulations, such as granules, a tablet, a capsule, and the like, for ingestion. Alternatively, a food supplement, such as a sports bar, nutraceutical, and the like, may be employed for delivery of the functionalized biopolymer compound.

The solid oral formulation, and other dosage forms as described herein, of the functionalized biopolymer compound may further include various controlled release formulations, as discussed previously. This may enhance its capabilities by enabling a "response" over a prolonged period of time. Thus, the functionalized biopolymer compound may be useful during activities (i.e., athletic events) which may initiate the inflammatory response in cells.

Other formulations, such as an emulsion, suspension, and the like, may be employed and allow delivery of the present invention to a desired location. The formulations may allow application through a variety of methods, such as a topical application, parenteral application, and the like. For example, topical functionalized biopolymer compounds may include lotions, creams, gels, and the like, and may be applied directly to a wounded or inflamed area. These organic compounds may further comprise penetrating agents, which may be employed to increase the bio-availability of the bioactive agent across a membrane, enhancing the topical functionalized biopolymer compound lipophilicity. Parenteral methods of delivering the functionalized biopolymer compound may include injections (subcutaneous or intravenous), suppositories (rectal or vaginal), and the like. Injections may comprise sterile solutions containing the functionalized biopolymer compound and may be delivered directly to the bloodstream or deposited in the inflamed tissue itself. The suppositories may contain suspensions, solids, or liquid formulations of the functionalized biopolymer.

For the delivery of drugs, the route of administration is dependent on the dosage form of a given drug. Thus, various dosage forms are known and contemplated for use by the current invention. For example, (1) Inhaled dosage forms: Aerosol, Gas, Inhaler & Metered dose inhaler, Solution for nebulizer; (2) Ophthalmic dosage forms: Eye drop (solution or suspension), Ophthalmic gel, Ophthalmic ointment; (3) Oral dosage forms: Capsule, Powerder, Solution, Suspension, Tablet, Buccal or sublingual tablet; (4) Otic dosage forms: Ear drop (solution or suspension); (5) Parenteral dosage form: Solution or suspension for injection; (6) Rectal dosage form: Enema, Suppository; (7) Topical dosage forms: Creams, Gel, Liniment, Lotion, Ointment, Paste, Transdermal Patch; (8) Vaginal dosage forms: Douche, Intrauterine device, Pessary (vaginal suppository), Vaginal ring, Vaginal tablet. There are also various types of Pharmaceutical forms which cover the way drugs are delivered to a patient and include, Ampules, Capsules, Creams, Elixirs, Emulsions, Fluids, Grains, props, Injections, Solutions, Lotions, Sprays, Powders, Suspensions, Syrups, Tablets, Tinctures, and Ointments. While some of these forms may be repetitive it is important to note that all the various dosage forms and delivery mechanisms are contemplated for use by the current invention.

As discussed previously, the functionalized biopolymeric matrix of the current invention may be employed to deliver bioactive agents, including bioactive proteins, such as platelet-derived growth factor (PDGF), epidermal growth factor (EGF) and basic fibroblast growth factor (bFGF) that may significantly accelerate the regeneration of damaged tissue, as well as vascular endothelial growth factor (VEGF) to promote growth of new blood vessels within the new tissue. These bioactive agents may be delivered by the current invention either alone or in combination with various other factors, drugs, biologics, cosmetics and otherwise. The mechanisms employed for delivery may be any of those previously discussed or alternative methods as contemplated by those skilled in the art.

In a still further preferred embodiment, the current invention may be employed for the detection of bacteria, viruses and other dangerous substances in various environments, such as hospitals, airplanes, and other commonly contaminated places. This sensing application may be realized by incorporating a functionalized film of the current invention into various devices, such as napkins, wet wipes, paper towels and the like as may be contemplated. Their use may be as simple as wiping any one of the various products incorporating the technology of the current invention across a surface. In a particularly preferred embodiment, antibodies may be loaded to the liposomes surface and chemicals are loaded either inside of the liposomes, onto the liposome surface, or, in the case of polydiacetylyene vesicles, the vesicle substituents themselves. The liposomes are anchored to the surface of the hm-Chitosan matrix, which makes the functional liposomes accessible by the contaminants. When the antibodies attach to their target they may trigger the chemical signal by changing color or through another detection/indication affect. Where biohazards are detected by the product of the current invention, the surface may be disinfected and retested with another "wipe" to insure no further contaminates exist.

The current invention further provides two novel systems. In a first system, the hm-Chitosan film matrix is presented for use. The use of this scaffold structure may be to functionalize it by loading vesicles whether or not including bioactive agents. The second exemplary, preferred embodiment of a system of the current invention may include the functionalized biopolymeric networked film being presented for use, such as within the fibrin mesh of a bandage or patch, in various environments as contemplated by those of ordinary skill in the art.

It is to be understood that the bioactive agents of the vesicles, for all of the exemplary, preferred embodiments described and those that are contemplated, may be any type of bioactive agent as contemplated. For instance, the agent may be various medications. Medications could be for: (1) the gastrointestinal tract or digestive system, (2) the cardiovascular system, (3) the central nervous system, (4) pain & consciousness (analgesic drugs), (5) musculo-skeletal disorders, (6) the eye, (7), the ear, nose and oropharynx, (8) the respiratory systems, (9) endocrine problems, (10) the reproductive system or urinary system, (11) contraception, (12) obstetrics and gynecology, (13) the skin, (14) infections and infestations, (15) immunology, (16) allergic disorders, (17) nutrition, (18) neoplastic disorders, (19) diagnostics, (20) euthanasia.

In the diagnosis arena, similar to the detection of bacteria and viruses, the current invention may employ various constructs such as antibodies to provide diagnostic capabilities.

Various different types of therapies may be promoted through the use of the current invention, such as hormone therapy whether amine-derived, peptide(s), and/or lipid and phospholipid-derived.

Still further, the current invention may be employed to store and deliver various proteins, such as enzymes which may include any of the (1) Oxidoreductases: catalyze oxidation/reduction reactions. (2) Transferases: transfer a functional group (e.g., a methyl or phosphate group), (3) Hydrolases: catalyze the hydrolysis of various bonds, (4) Lyases: cleave various bonds by means other than hydrolysis and oxidation, (5) Isomerases: catalyze isomerization changes within a single molecule, or (6) Ligases: join two molecules with covalent bonds.

In the agricultural and/or botanical fields, the current invention may be employed for the delivery of various agents for various products, including insecticides, fertilizer, and the like. Insecticides may vary from agricultural (e.g., organochlorides, organophosphates, pyrethroids, biological insecticides) to individual insecticides (e.g., chlorinated hydrocarbons, organophosphorus, carbamates, phenothizine, pyrethroids, plant toxin derived). The current invention may be employed for use with various herbicides (organic or inorganic) which may be classified either by activity (e.g., Contact or Systemic), use (e.g., Soil-applied, Pre-plant incorporated, Preemergent herbicides, Post-emergent herbicides), or mechanism of action (e.g., ACCase inhibitors, ALS inhibitors, EPSPS inhibitors, Synthetic auxin, Photosystem II inhibitors). Another field of application of the current invention may be Fertilizers and/or Manure whether they are classified as organic or inorganic fertilizers or green manures or animal manures.

The current invention also provides a preferred embodiment, wherein the novel hm-Chitosan and/or functionalized film may be deployed in a kit. For example, the kit may be a detection/diagnostic kit and include a collection of "wipes" (described previously) and an instruction manual for the proper use of the wipes for the determination of whether or not a contaminate, disease, virus, or otherwise is present. Various other types of products employing the technology of the current invention may be included within a kit as is contemplated by those of ordinary skill in the art. For example, a diagnostic kit may include a solution containing various antibodies to antigens presented by certain diseases or viruses. By collecting a sample and placing it in contact with the solution of the kit, and preferably in accordance with an instruction manual provided with the kit, a user may be able to detect or identify the presence of a disease or virus. Other examples of kits, such as prognostic indicator kits, assaying kits, and the like, employing the novel invention of the instant application are contemplated and fall within the scope and spirit of the present invention.

In the exemplary embodiments, it is understood that the specific order or hierarchy of steps in the methods disclosed are examples of exemplary approaches. Based upon preferences, it is understood that the specific order or hierarchy of steps in the method can be rearranged while remaining within the scope and spirit of the present invention. The accompanying method claims present elements of the various steps in a sample order, and are not necessarily meant to be limited to the specific order or hierarchy presented.

It is to be understood that the functional capabilities of the current invention, including those provided within the methods described, may be implemented in various manners. It is contemplated that various functional features may be individually provided to the system of the present invention. Further, the specific order or hierarchy of functional capabilities described herein are merely exemplary approaches and based upon design preferences may be rearranged while remaining with the scope and spirit of the present invention. The methods may employ the above described functional capabilities in various ways, enabling one or many of the features without regard to any specific hierarchical order.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A chitosan sponge-like film, comprising: one or more hydrophobic moieties covalently attached to the chitosan, wherein said chitosan sponge-like film is lyophilized.

2. The film of claim 1, wherein one or more hydrophobic moieties have a molecular formula of $C_{12}H_{25}$.

3. The film of claim 1, wherein said one or more hydrophobic moieties comprise n-alkyl functional groups.

4. The film of claim 1, wherein the chitosan sponge-like film adheres to lipid or surfactant bilayers through hydrophobic interactions.

5. The film of claim 1, wherein <10% of available amines in the chitosan are occupied by the one or more hydrophobic moieties.

6. The film of claim 1, wherein the one or more hydrophobic moieties are organic compounds with a backbone of at least six and no more than thirty six carbon atoms.

7. The film of claim 1, further comprising a vesicle.

8. The film of claim 7, wherein the vesicle is functionalized with at least one bioactive agent.

9. A biopolymeric film, comprising:
a bioactive chitosan sponge-like film comprising one or more hydrophobic moieties covalently attached to the chitosan, wherein said chitosan sponge-like film is lyophilized and wherein said film includes nano-compartmentalized vesicles loaded with bioactive agent, the vesicles bound to hydrophobically modified chitosan scaffolds through the hydrating of the lyophilized film of hydrophobically modified chitosan scaffolds with a solution of the vesicles.

10. The film of claim 9, wherein the bioactive agent is selected from the group consisting of biologically active molecules, moieties, or compounds, pharmacologically active compounds, drugs, medicines, cosmetics, phylogenically/botanically active molecules and compounds, herbicides, pesticides, or insecticides.

11. A kit, comprising:
a lyophilized chitosan sponge-like film comprising hydrophobic moieties, and one or more vesicles comprising bioactive agents, wherein said vesicles are capable of attaching to said hydrophobic moieties.

12. The kit of claim 11, wherein said vesicles comprising bioactive agents are capable of being released from the film upon interaction with an environment.

13. A method of fabricating a biopolymeric film, comprising: covalently binding a chitosan biopolymer with amphiphilic, organic compounds; and dehydrating the hydrophobically modified biopolymer into a solid state film through a lyophilization process.

14. The method of claim 13, further comprising the step of hydrophobically interacting the solid-state, hydrophobically modified biopolymer with a plurality of vesicles.

15. A method of using a hydrophobically modified biopolymer film, comprising:
hydrophobically interacting a chitosan sponge-like film, comprising one or more hydrophobic moieties covalently attached to the chitosan, wherein said chitosan sponge-like film is lyophilized, with vesicles loaded with bioactive agents and allowing the self-assembly of a functionalized biopolymeric networked film with the vesicles.

16. The method of claim 15, wherein the hydrophobic interaction occurs via various processes selected from the group consisting of soaking, passing over, and immersion.

17. The method of claim 15, wherein prior to the interacting step the method further includes steps selected from the group consisting of removing the film from the material it was cast upon, storing the film, and retrieving the film from storage.

18. The method of claim 15, further comprising the step of applying a functionalized biopolymeric networked film to a location of need either by direct or indirect application.

19. The method of claim 18, wherein the direct delivery occurs by application of the film to a wounded area.

20. The method of claim 15, wherein the film may be loaded onto at least one of a therapeutic device, pharmacological device, cosmetic device, and agricultural device.

21. The film of claim 1, wherein the one or more hydrophobic moieties are covalently attached to one or more amino groups on the chitosan film.

* * * * *